United States Patent
Travish et al.

(10) Patent No.: US 11,127,174 B2
(45) Date of Patent: Sep. 21, 2021

(54) MEDICAL IMAGING SYSTEM WITH A FIXED ARRAY OF X-RAY DETECTORS AND A FIXED ARRAY OF X-RAY EMITTERS FOR PRODUCING A DIGITAL 3-DIMENSIONAL IMAGE

(71) Applicant: Adaptix Ltd, Oxfordshire (GB)

(72) Inventors: Gil Travish, Oxford (GB); Raphael Hauser, Oxford (GB); Kishan Patel, Greater London (GB)

(73) Assignee: ADAPTIX LTD., Oxfordshire (GB)

( * ) Notice: Subject to any disclaimer, the term of this patent is extended or adjusted under 35 U.S.C. 154(b) by 677 days.

(21) Appl. No.: 16/071,624

(22) PCT Filed: Jan. 25, 2016

(86) PCT No.: PCT/IB2016/000637
§ 371 (c)(1),
(2) Date: Jul. 20, 2018

(87) PCT Pub. No.: WO2017/130018
PCT Pub. Date: Aug. 3, 2017

(65) Prior Publication Data
US 2021/0209818 A1    Jul. 8, 2021

(51) Int. Cl.
*A61B 6/00* (2006.01)
*G06T 11/00* (2006.01)
(Continued)

(52) U.S. Cl.
CPC ............ *G06T 11/006* (2013.01); *A61B 6/025* (2013.01); *A61B 6/4085* (2013.01);
(Continued)

(58) Field of Classification Search
CPC .......... G01N 23/04; H05G 1/38; A61B 6/025; A61B 6/4085; A61B 6/4233; A61B 6/583
See application file for complete search history.

(56) References Cited

U.S. PATENT DOCUMENTS

2015/0228092 A1* 8/2015 Claus ................... A61B 6/5205
382/131

FOREIGN PATENT DOCUMENTS

| EP | 2269511 A1 | 1/2011 |
| EP | 2269511 A1 | 5/2011 |

(Continued)

OTHER PUBLICATIONS

International Searching Authority, International Search Report, PCT/IB2016/000637, dated Nov. 4, 2016.
(Continued)

*Primary Examiner* — Dani Fox
(74) *Attorney, Agent, or Firm* — Reichel Stohry Dean LLP; Mark C. Reichel; Natalie J. Dean

(57) ABSTRACT

The individual emitters are operated in multiple groups each illuminating a region of interest between the emitter array and the detector array such that the cone of radiation rays projected on the detector array from any single emitter in any one such group is substantially spatially separated from the corresponding projected cones from all other emitters in that same group. At least the ROI portion of the 3D space between the emitter panel and the detector panel is represented by 3D volume elements (voxels), wherein at least some of those voxels represent respective portions of that space that are traversed by corresponding portions of a plurality of radiation rays each extending from a respective emitter to a respective detector and are associated with respective absorption coefficients representative of the radiation absorption characteristic of a corresponding portion of the ROI. The image reconstruction process is an iterative process in which neighboring voxels having similar calculated coefficients are combined into larger voxels, neighboring voxels having dissimilar calculated coefficients (Continued)

are divided into smaller voxels, and new absorption coefficients are calculated.

27 Claims, 16 Drawing Sheets

(51) Int. Cl.
*A61B 6/02* (2006.01)
*G06T 5/00* (2006.01)

(52) U.S. Cl.
CPC ............ *A61B 6/4233* (2013.01); *A61B 6/583* (2013.01); *G06T 5/002* (2013.01); *G06T 11/008* (2013.01); *G06T 2207/10116* (2013.01); *G06T 2207/20064* (2013.01); *G06T 2207/30004* (2013.01)

(56) References Cited

FOREIGN PATENT DOCUMENTS

| | | |
|---|---|---|
| JP | 2000051204 A | 2/2000 |
| JP | 2010-069012 A | 4/2010 |
| WO | 2015157497 A2 | 10/2015 |
| WO | 2015/167308 A1 | 11/2015 |

OTHER PUBLICATIONS

International Searching Authority, Written Opinion of the International Searching Authority PCT/IB2016/000637, dated Nov. 4, 2016.
Brazilian Patent and Trademark Office, Search Report for Application No. BR1120180512-1, dated Aug. 20, 2020.
Japanese Patent Office, Notice of Reason of Refusal for Application No. 2018-537849, dated Dec. 10, 2019.

* cited by examiner

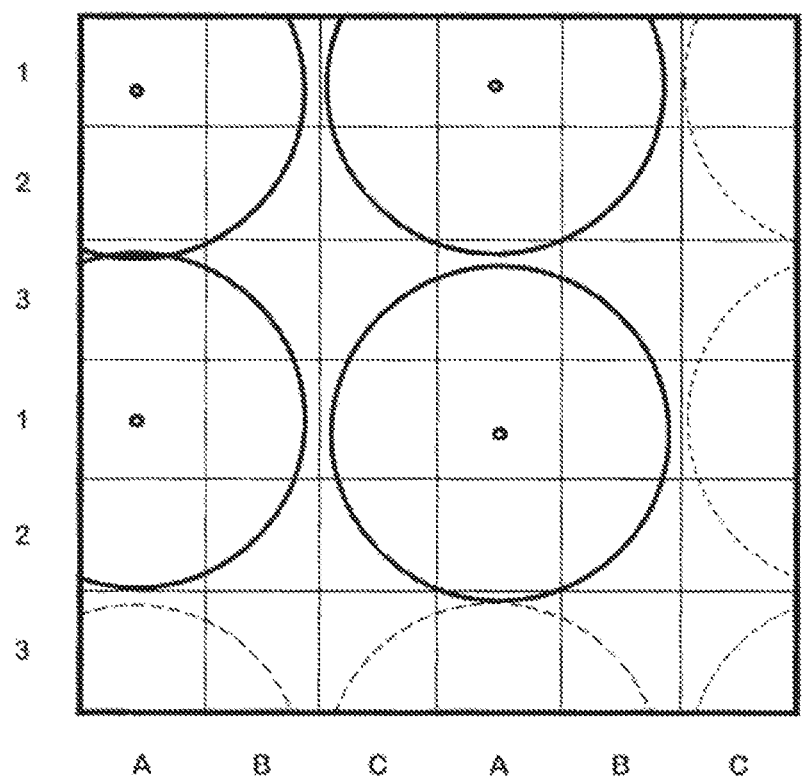
Fig 5.1.A

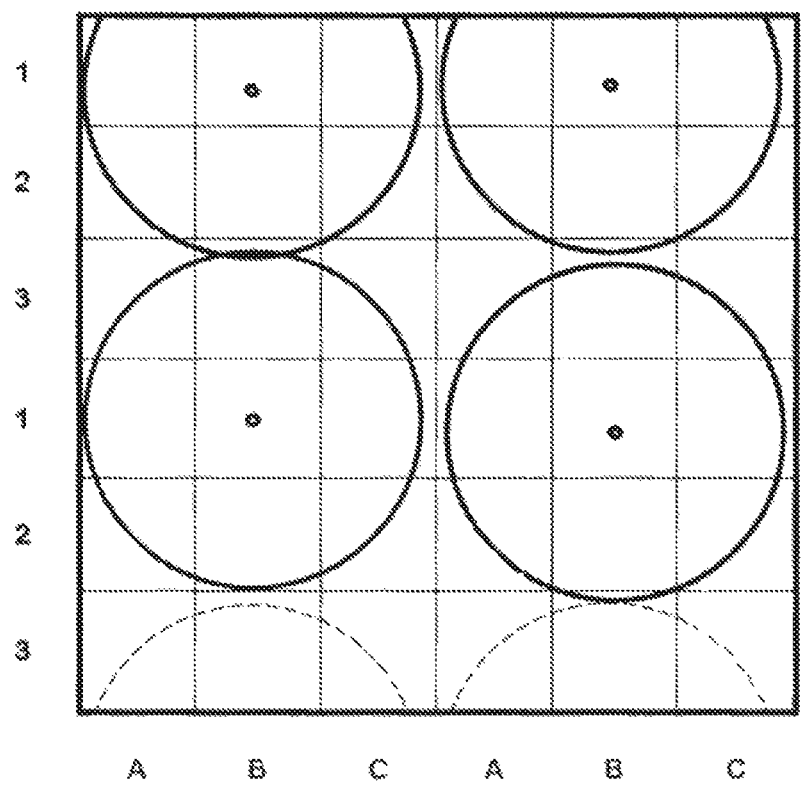
Fig 5.1.B

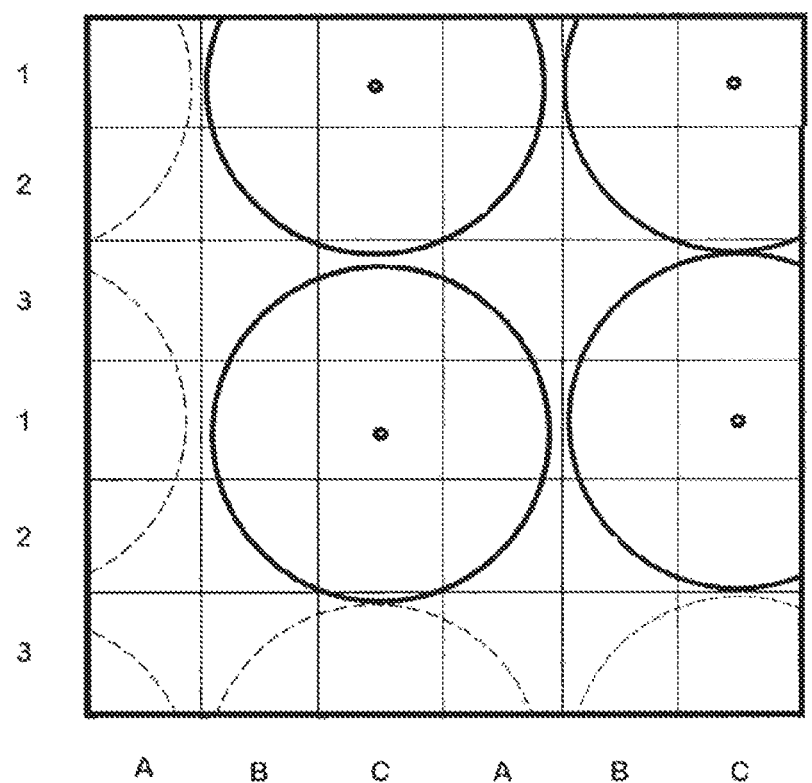
Fig 5.1.C

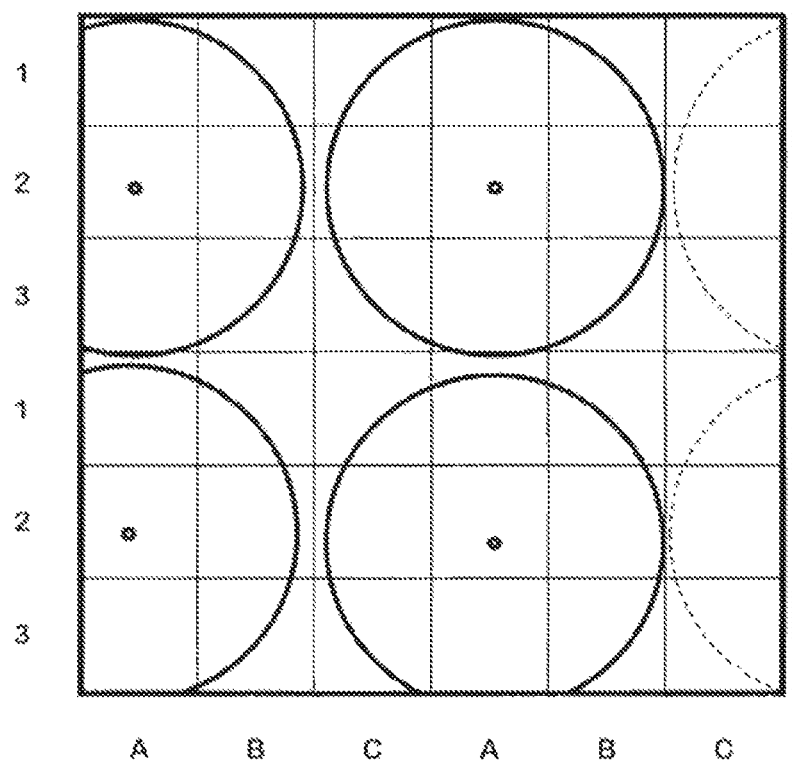
Fig 5.2.A

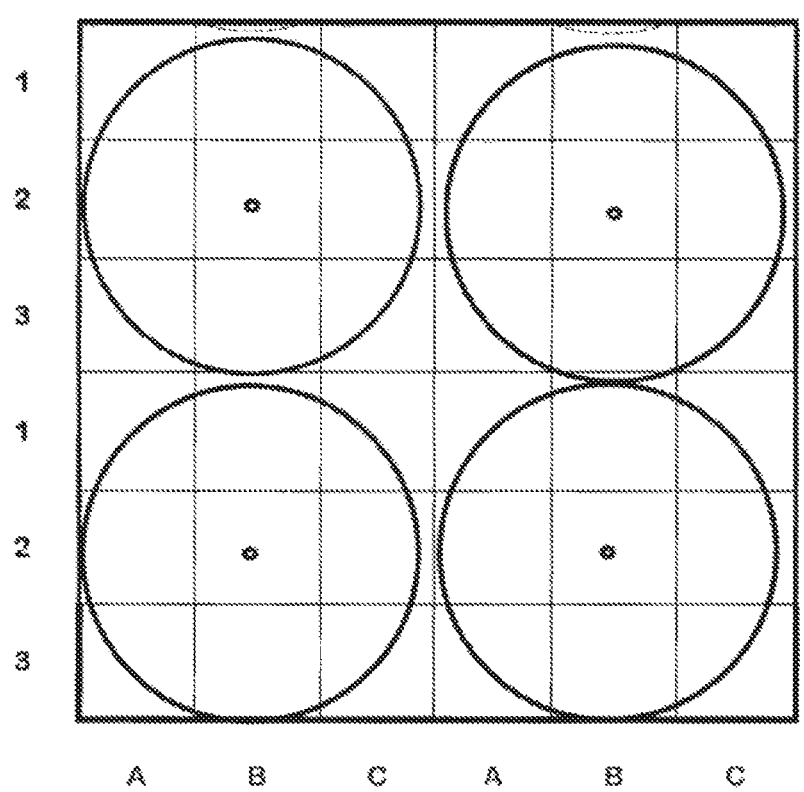
Fig 5.2.B

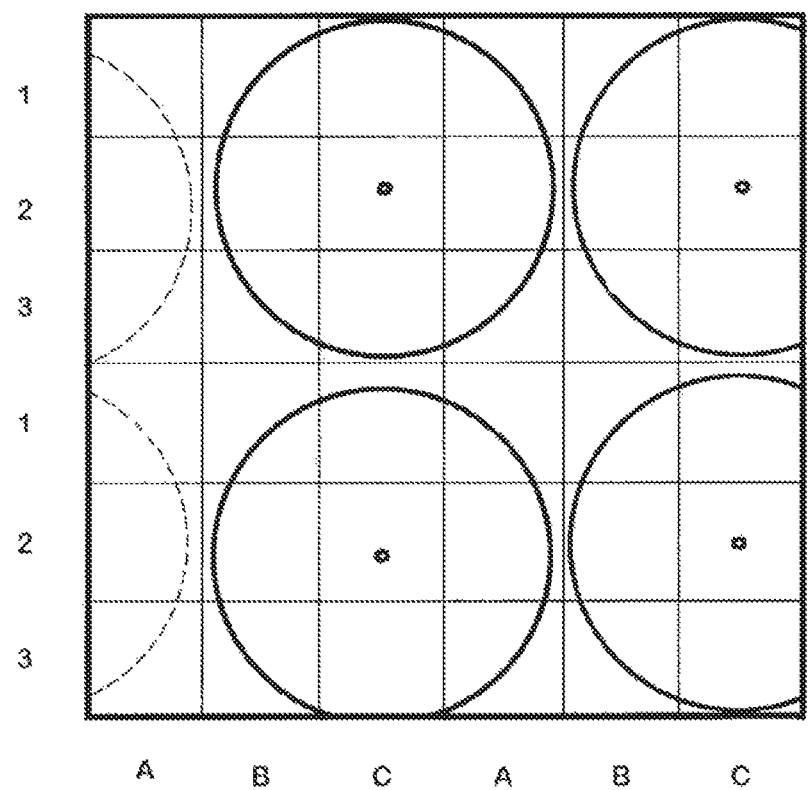
Fig 5.2.C

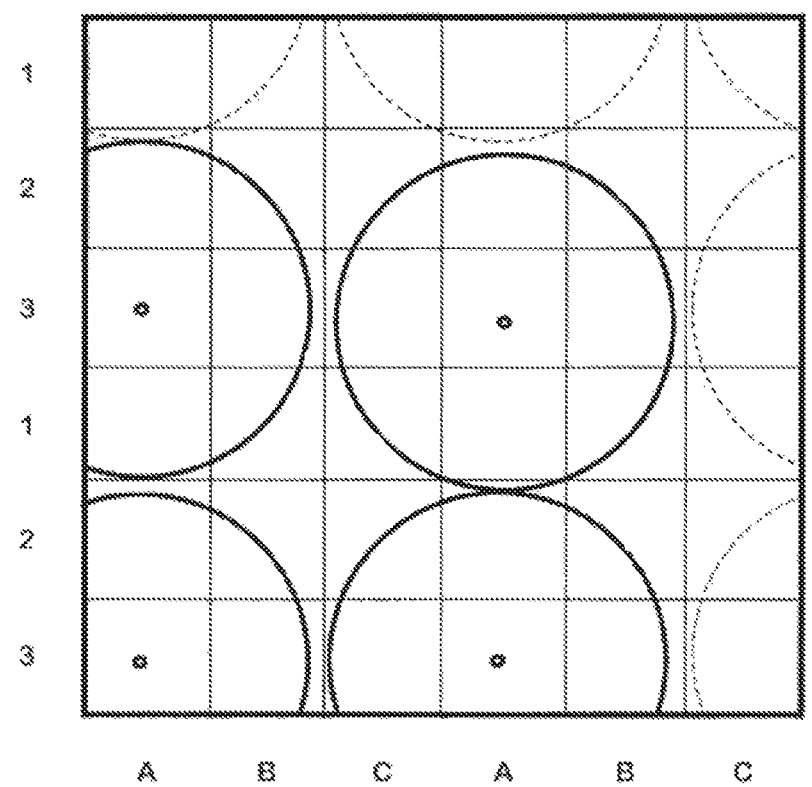
Fig 5.3.A

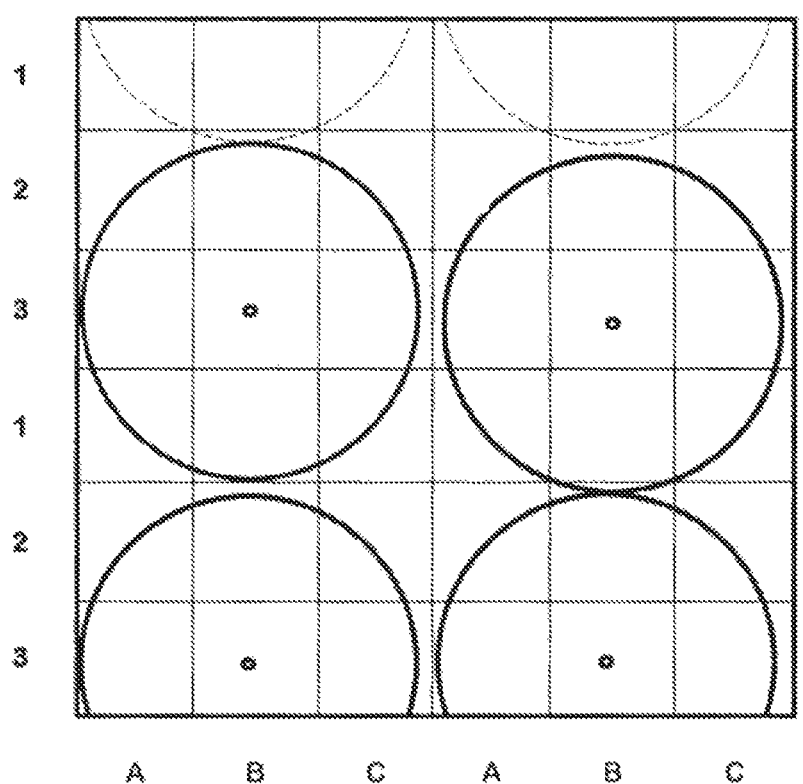
Fig 5.3.B

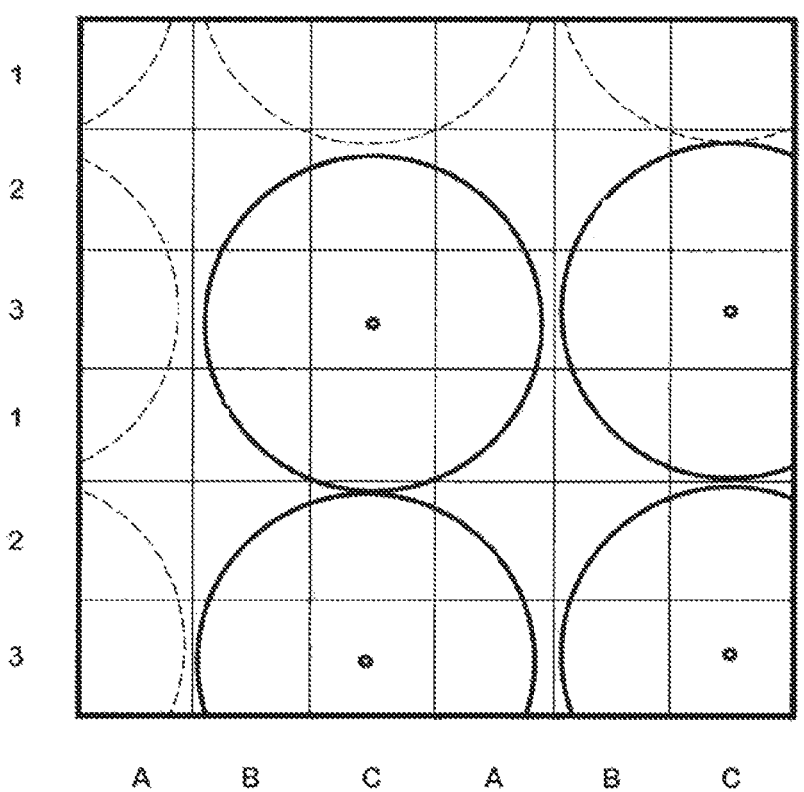
Fig 5.3.C

MEDICAL IMAGING SYSTEM WITH A FIXED ARRAY OF X-RAY DETECTORS AND A FIXED ARRAY OF X-RAY EMITTERS FOR PRODUCING A DIGITAL 3-DIMENSIONAL IMAGE

PRIORITY

The present application is related to, and claims the priority benefit of, and is a 35 U.S.C. 371 national stage application of, International Patent Application Serial No. PCT/IB2016/000637, filed Jan. 25, 2016, the contents of which are hereby incorporated by reference in their entirety into this disclosure.

BACKGROUND ART

A digital x-ray imaging system will typically comprise:
An object to be imaged (e.g. an internal Region of Interest of a patient);
A source used to transmit x-rays having a predetermined intensity (flux);
A detector for receiving the x-rays and outputting the received flux as raw digital output data;
A support for holding, moving and/or aligning the source and the detector relative to the object being imaged such that at least some of the transmitted flux passes through the object before it is received by the detector;
A digital controller for controlling the flux transmitted by the source before it reaches the object;
A digital processor for storing and analyzing the raw output data from the detector to produce digitized image data representative of variations of a predetermined physical characteristic within the object being imaged; and
A display device for presenting the image data in a form intelligible to a human operator.

The two dimensional (2D) images (radiographs) used in most medical radiography are created directly from differential attenuation of the applied radiation passing through a subject. Because biological subjects are semi-transparent to x-rays of sufficiently high energy and intensity, the resultant "shadow" image combines information about all the tissues between the source and the detector. Those 2D radiographs typically use a cone-shaped beam of X-rays from a single point source that is projected onto a flat plane of analog film or a planar array of digital detectors, leading to substantial geometric distortion and parallax effects in the resultant grayscale images, which require skilled human interpretation to convert into a medically meaningful diagnosis.

The distance between the source and the object (eg a particular internal organ or orthopedic structure) to be imaged is known as the source to object distance (SOD), and is a function of the angle of the X-ray cone and a desired coverage width of the object. In practice the SOD is further constrained by the so-called skin safe distance, as the X-rays must not cause an excessive dose where they enter the portion of the patient's body adjacent the source. The magnification of the received image is governed by the ratio of the source to object distance (SOD) to the source to image distance (SID), that is, the distance between the point source and the image receiver (typically a two dimensional detector panel or photosensitive film) that measures the radiation that is not absorbed by the object (the person, animal or object to be imaged).

Conventional Computed Tomography (CT) uses a moving source, collects many (essentially all) projections through the subject, and constructs a digital image by a direct algorithmic transformation of the collected data, described mathematically as applying the inverse Radon transform. CT scans collect much more data and involve significantly higher overall doses than 2D radiographs.

Digital Tomosynthesis (DT) utilizes a more limited sweep angle than CT and produces an effective dose to a patient for a Chest X-Ray (CXR) substantially less than that of a Low Dose chest CT and typically only about 30% more than a conventional two-view chest radiography examination.

High-resolution limited-angle tomography (Tomosynthesis) is a relatively new technology currently being used for mammography that minimizes the overlap of tissues in the projected image present in conventional shadow radiography, but with a lower dose and less complicated equipment than that required for CT, and still permits the radiologist to discriminate between an apparent abnormality and the anatomical structures above and below it. The actual algorithms for Tomosynthesis are well documented and typically involve ACT/Radon methods.

When multiple images of an object are to be obtained from a variety of directions from which a three dimensional image may be reconstructed, a mechanical gantry may be used to move a single source along a sequence of locations relative to the object.

More recently it has been proposed to use a static two dimensional array of emitters facing a corresponding array of detectors to produce a 3D image. However, if the region of interest includes multiple tissue types having a range of densities and the data is to be made available in real time to medical personnel without exposing the patient to potentially harmful levels of radiation, the use of both a spatially distributed fixed emitter array and a spatially distributed fixed detector array to reconstruct an accurate three dimensional image presents new challenges, particularly in the development of appropriate scanning and data capture processes that provide statistically sufficient image data with minimal radiation exposure to the patient, and in the efficient processing of that data to calculate and display selected views of the region of interest while the patient is still available for any indicated radiological follow up.

DISCLOSURE OF INVENTION

The positions of a 2D emitter array and a 2D detector array are determined relative to a 3D coordinate reference system.

The individual emitters are organized in multiple groups each illuminating a region of interest between the emitter array and the detector array such that the cone of radiation rays projected on the detector array from any single emitter in any one such group is substantially spatially separated from the corresponding projected cones from all other emitters in that same group.

In some embodiments the organization of emitters into groups is based on regular geometrical patterns such as extended arrays of regular polygons (e.g. squares or equilateral triangles) with the emitters in each group being associated with vertices or centers of individual polygons that are separated by a predetermined distance corresponding to the nominal diameter of the projected radiation cone, and with a similar organization of the other groups but with respective predetermined offsets that are multiples of a fraction of that nominal diameter.

In other embodiments the organization of emitters into groups may be preceded by a calibration step that identifies the projection pattern of each emitter on the individual detectors, and that ensures that each emitter in a particular group has a respective projection pattern that does not interfere with the accurate detection of radiation from any other emitter of that same group and that each operational detector receives radiation from at least a predetermined number of emitters. In one particular such embodiment, a pseudo random process is used to select the emitters in each group.

Each such group of emitters is operated during different respective time intervals, thereby achieving substantial temporal separation of radiation from more than one emitter within the effective field of view of the same detector, whereby radiation received by a specified detector during a specified interval of time can be directly correlated with the radiation transmitted during that same interval of time by a specified emitter.

In a presently preferred embodiment particularly adapted for medical imaging purposes, the coordinate system including the approximate location of a region of interest (ROI) of the patient relative to the emitter and detector arrays is determined prior to any radiation exposure. Moreover, the patient is positioned an appropriate distance from the successively activated emitters to ensure that every point within the ROI receives radiation from at least three (and preferably more than three) non-collinear emitters.

The intensity of the radiation received by each detector during each such specified interval of time is measured and stored in an input data matrix, whereby the input data matrix will collectively contain sufficient information required to reconstruct (render) a representation (phantom image) of the ROI disposed between the emitter panel and the detector panel.

At least the ROI portion of the 3D space between the emitter panel and the detector panel is represented by an initial output data matrix of 3D volume elements (voxels), wherein at least some of those voxels represent respective portions of that space that are traversed by corresponding portions of a plurality of radiation rays each extending from a respective emitter to a respective detector and are associated with respective absorption coefficients representative of the radiation absorption characteristic of a corresponding portion of the ROI.

In certain embodiments, the initial dimensions of the voxels, the initial values of the associated coefficients, and/or the location of the various portions of the ROI relative to the emitters and detectors may be derived from a prior radiological examination of the same or an analogous ROI.

Respective absorption coefficients and associated errors are calculated for each voxel in an image reconstruction process that employs computationally efficient voxelation and ray tracing procedures based on the stored intensity information for each received radiation ray that passes through that voxel from each emitter to each detector, thereby transforming the input data matrix of received intensity data into an output data matrix of voxels each having a calculated absorption coefficient and an associated error.

In certain embodiments, the image reconstruction process may also take into account any known physical attributes of the ROI such as the relative proportion of different tissues having different absorption coefficients, and the probable size, shape and location of tissue having similar absorption coefficients.

The image reconstruction process is an iterative process in which the existing output data matrix is replaced with a new output data matrix wherein voxels having similar calculated coefficients with their immediate neighbors have been combined into larger voxels, voxels having dissimilar calculated coefficients from their immediate neighbors have been divided into smaller voxels, and new absorption coefficients are calculated with new calculated errors.

The iterative process is repeated until a defined limit has been reached.

In some embodiments, the defined limit is based on the extent to which the new iteration represents a significant improvement over the prior iteration.

In some embodiments, the defined limit is reached only after the combination or division of voxels fails to reduce the calculated error within a predetermined level of confidence.

In some embodiments, the defined limit includes a maximum allowable time for creating new output data matrices.

In a presently preferred embodiment, the iterative process starts with a matrix having relatively few voxels (for example 4×4×4=64 voxels) and subsequently expands the number of voxels (or equivalently, reduces the volume of each voxel) only in those regions that have been identified in a prior iteration as having a statistically high absorption coefficient and/or a statistically significant change in absorption coefficient relative to coefficients in nearby regions.

In certain other embodiments, the iterative process starts with a matrix having a relatively large but still computationally practical number of voxels (for example not more than 100×100×100=1,000,000 voxels) and increases the number of voxels in one region (for example by spitting n voxels in half to produce n additional voxels) only after a corresponding reduction has been made in another region (for example, by combining n+1 adjacent voxels into one super voxel).

The locations of the individual voxels and their calculated absorption characteristics in the final 3D output data matrix may then be transformed into a specified 2D view (or series of views) of the phantom image.

In certain practical applications, the deviation of coefficients of the immediate neighbors may be suggestive of a curved boundary, which can be detected and refined by known methods.

In other practical applications, the deviation of individual coefficients of the surrounding neighboring voxels may be suggestive of an artifact which is resolved by subsequent refinement of the affected voxels.

Not all the above functionalities will be required for every possible embodiment of the invention, nor will those functions necessarily be performed in the order set forth above. For example, if the emitter array and the detector array are coupled together with a sufficiently rigid structure, then the fixed coordinate system and the distance between the two arrays can be determined at time of manufacture and prior to any practical use of the imaging device. In another example, the transformation of the voxel data into a specified view of the ROI could be replaced by simply outputting the calculated voxel data, which could then be normalized and compared statistically with comparable data from other subjects having known characteristics (such as the presence or absence of a predetermined disease or other medical condition) to determine a numerical test score indicative of the probability of the presence or absence of a particular disease or deficiency or other defined characteristic in the ROI undergoing examination.

Although it is contemplated that most of the above mentioned functions will be implemented by means of one or more programmed digital computers, at least some of those functions could be performed by a human operator (for example, the verification of the relative position of the ROI with respect to the emitters and the detectors), and others could be performed by dedicated hardware (for example, the sequential operation of the emitters). Moreover, some of the required functionality may be operational only when the apparatus is being manufactured or repaired or during periodic inspection and maintenance, and other functionality may be operational only once during a sequence of multiple radiological examinations involving multiple patients.

DRAWINGS

FIG. 5 comprising FIGS. 5.1A through 5.3C shows 9 views of a single 6×6 array illuminated by a regular arrangement of 9 different overlapping radiation patterns each having a diameter approximately equal to the lateral dimension of a single 3×3 subarray such that the radiation patterns in any one such group do not overlap.

Figure 6A:
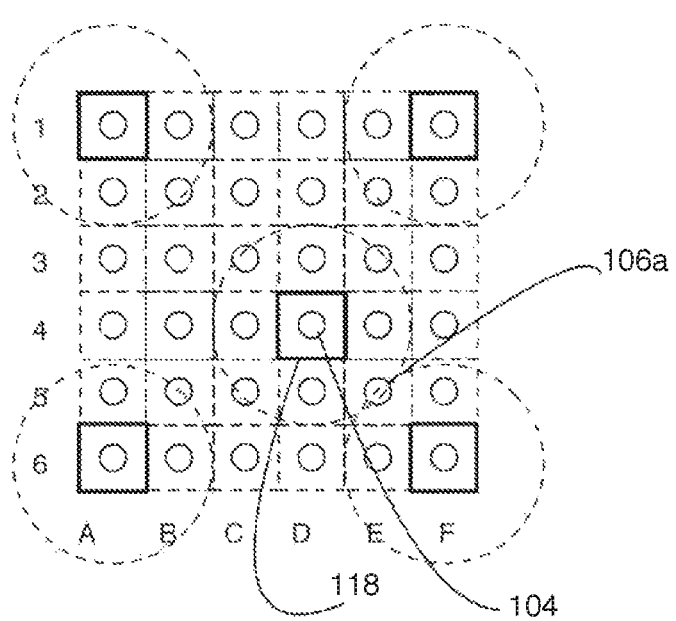
Figure 6B:
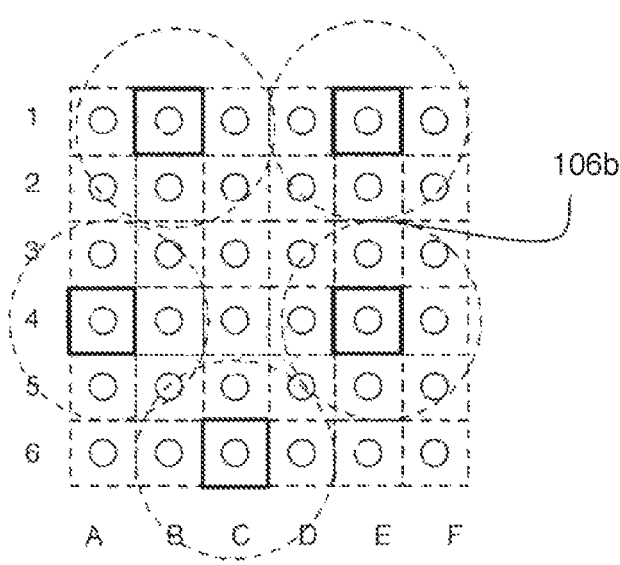

FIG. 6 comprising FIGS. 6A and 6B shows how the emitters of a single 2-dimensional array may be logically divided into a plurality of pseudo randomly selected groups such that the respective coverage areas of the emitters in any such group do not overlap.

Figure 1:
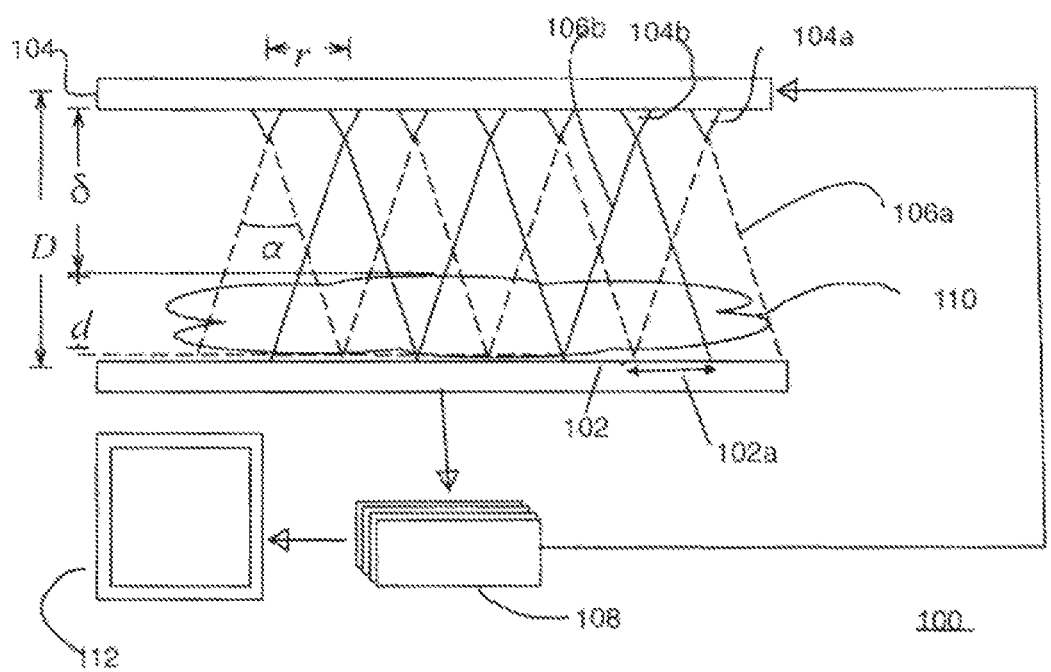
FIG. 1 shows the basic subsystems of an exemplary medical imaging system having a fixed array of x-ray detectors and a fixed array of x-ray emitters, and shows how adjacent emitters project overlapping beams of radiation on the same area of the detector array if operated simultaneously.
Figure 7:
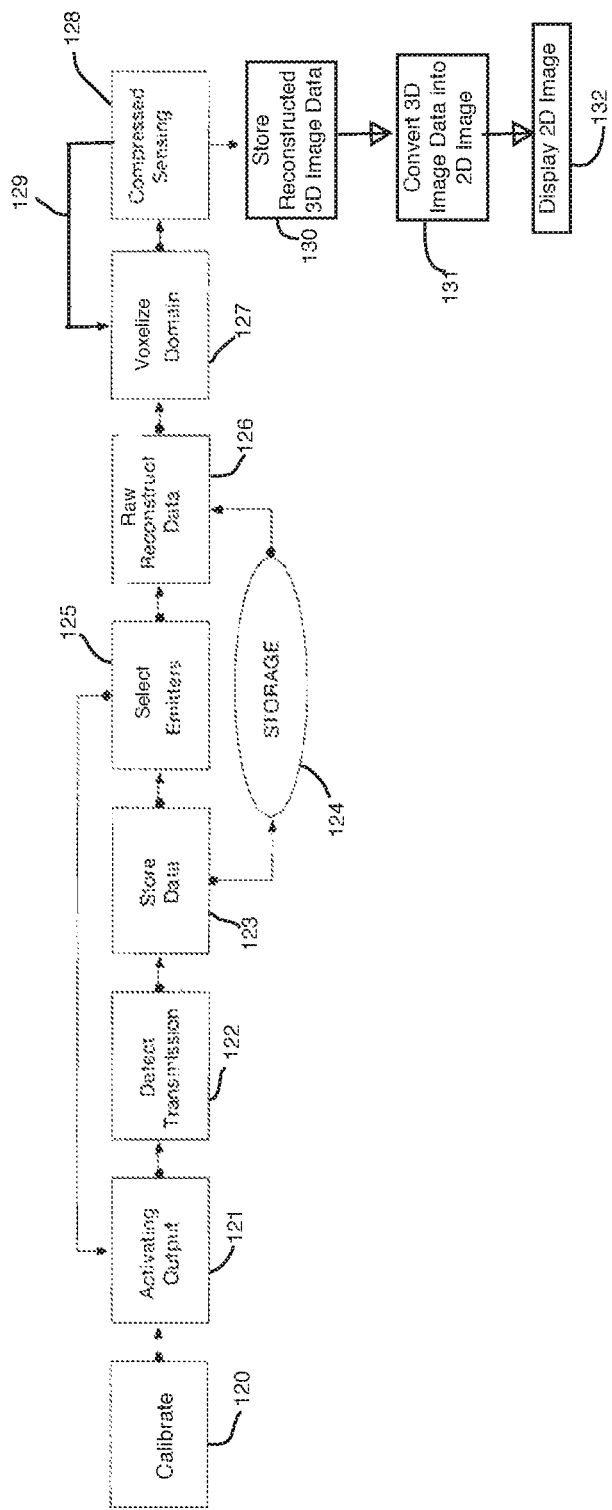

FIG. 7 is a functional flow diagram of certain key processes performed by the imaging system of FIG. 1.

DESCRIPTION OF EXEMPLARY EMBODIMENT(S)

A detailed description of an exemplary architecture and design methodology for a novel miniaturized X-ray panel particularly suitable for use with the present invention is disclosed and claimed in commonly assigned unpublished PCT application PCT/IB2015/057792 filed on 12 Oct. 2015 and entitled A METHOD OF DESIGNING AN X-RAY EMITTER PANEL. A copy of the Specification and Drawings of that application is attached hereto as Appendix A, and said application is hereby incorporated by reference in its entirety.

Reference should now be made to FIG. 1, which shows the basic subsystems of an exemplary medical imaging system 100 having a fixed array of x-ray detectors 102 and a fixed array of x-ray emitters 104, in which adjacent emitters 104a 104b may project overlapping beams 106a 106b of radiation onto the same area 102a of the detector array 102 if operated simultaneously. As shown in FIG. 1, imaging system 100 also includes an acquisition workstation 108 which controls the radiation from the individual emitters 104a 104b (or groups of emitters) forming emitter array 104 and transforms the output data from the detector array 102 into a three dimensional array of data representing the radiation attenuation coefficient (i.e., the local density) at each point within an object being examined 110 (the "Region of Interest" or "ROI"). Visualization workstation 112 performs the calculations necessary to transform the image data from acquisition workstation 108 into one of more internal views of ROI 110 that are displayed to a radiologist or other medical professional.

In order to carry out the specific attenuation coefficient calculations performed by workstation 108 and described in further detail hereinafter with respect to FIG. 7 below, the relative position (distance and orientation) of each detector within the projection cone of each emitter on the two respective panels 102, 104 of the imaging system has to be determined. Equivalently, since the positions of emitters on the emitter panel 104 and the positions of detectors on the detector panel 102 are fixed at time of manufacture and thus known a priori, only the relative position of the two panels 102, 104 with respect to each other needs to be measured. Using one of the two panels as a reference system, with a specified point (e.g., one of its corners in the case of a rectangular panel) as the origin and with two fixed orthogonal coordinate axes lying in the plane of the panel defining the position and orientation of the x- and y-axes, the normal to that first panel plane fixes a z-axis. The position of the second panel relative to this fixed coordinate system may then be determined by measuring the coordinates of three fixed points in the plane of the second panel (e.g., three of its corners, in the case of a rectangular panel). This requires six numbers (or coordinates), taking into account that the lengths of the distances between the three points and the angles between their connecting line segments are known. From these six numbers the relative positions of all emitters and detectors can be computed, using basic analytic geometry. For a fixed installation, the required measurements will be made when the apparatus is installed, as part of the installation process, and verified during routine scheduled maintenance. Alternatively, the six required coordinates may be determined with respect to a known "test probe" placed in a known position during daily system verification and calibration, or measured mechanically or via actuators during system start up and initialization, and/or re-calibrated before each set sequential exposures of a particular ROI.

Figure 2:
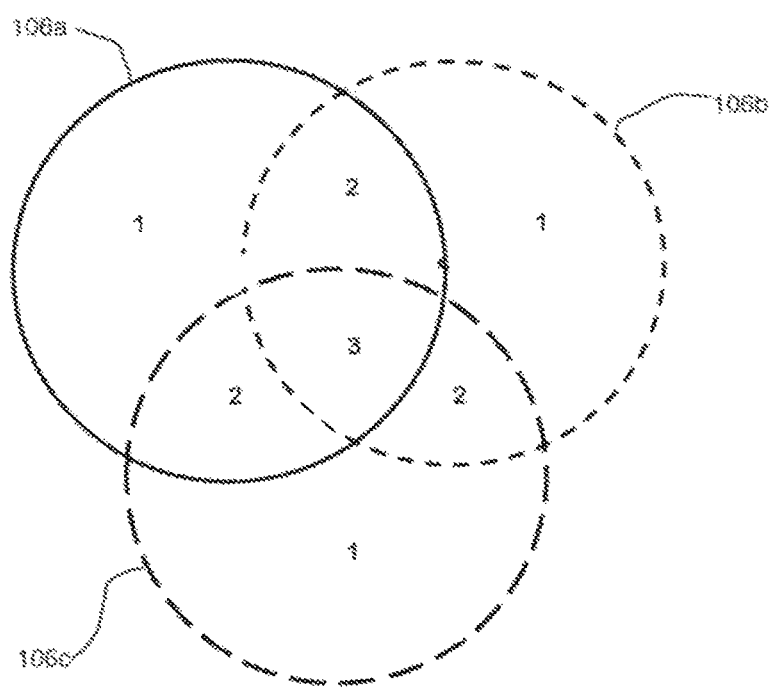
FIG. 2 is a diagrammatic plan view of a portion of the detector panel of FIG. 1 showing radiation patterns from three adjacent emitters projected onto overlapping areas of the detector panel.

Reference should now be made to FIG. 2, which is a diagrammatic plan view of a portion of the detector panel of FIG. 1 showing radiation patterns from three adjacent emitters projected onto corresponding partially overlapping areas 106a, 106b, 106c of the detector panel. To maximize the amount of information available for a given dose and exposure time (and as described in more detail in the referenced commonly assigned PCT application), sets of emitters with only limited spatial overlap can be arranged to emit radiation simultaneously, and emitters that produce overlapping cones of radiation can be individually controlled to emit radiation in succession, so as to achieve temporal separation. In this process, each emitter produces an image or shadow of any objects (or portions thereof) within the projection cone which the emitter projects on the detector panel, and the information contained in those images or shadows and captured by the individual detectors during successive bursts of radiation is available to render a 3D model of the ROI (as disclosed in more detail hereinafter with reference to FIG. 7). As indicated by the numeral "3", all three emitters have coverage in the central area, while each pair of emitters has an overlapping coverage area (numeral "2") within the intersection of their respective coverage areas (and also with that of the third emitter, indicated by the numeral "3"). In contrast, the outlaying portions (numeral "1") of the combined coverage area are covered only by one emitter.

Figure 3:
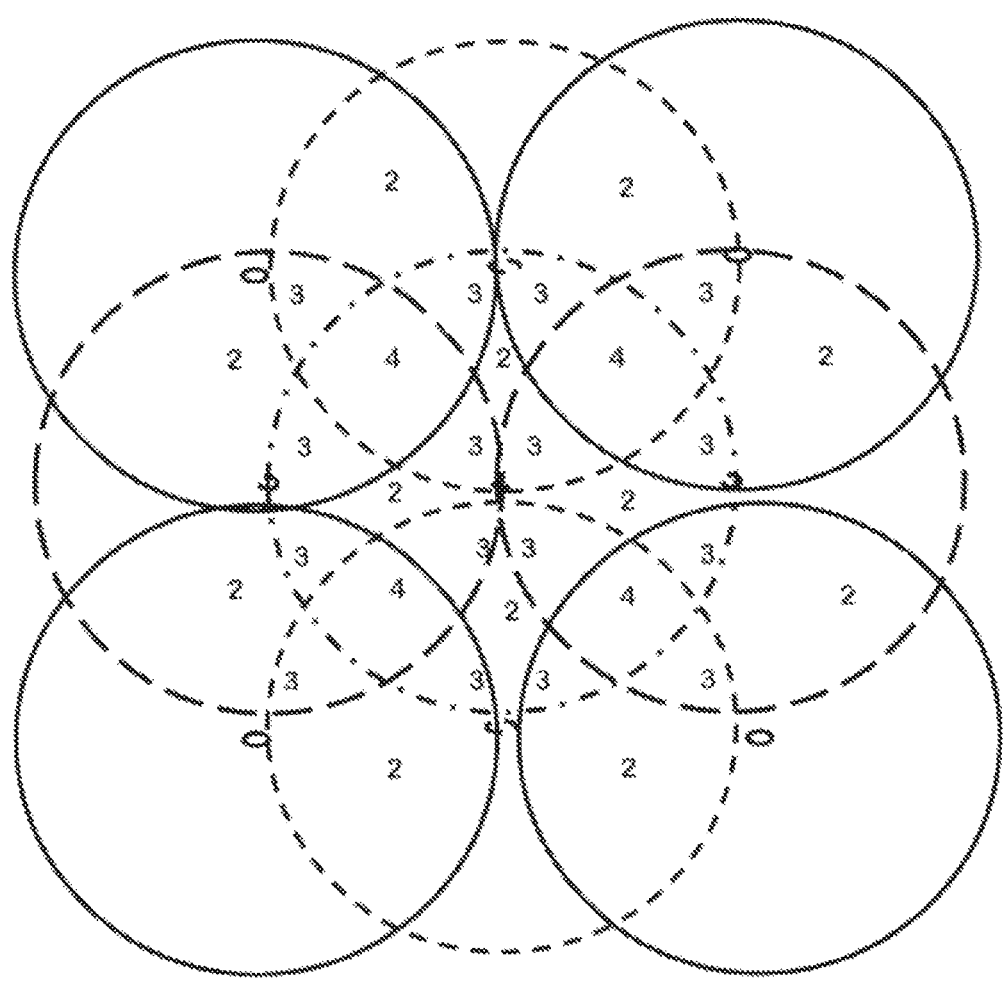
FIG. 3 is similar to FIG. 2, but shows the improved coverage overlap resulting from eight emitters surrounding a ninth emitter.

FIG. 3 is similar to FIG. 2, but shows the improved overlap (represented by the numerals "1", "2", "3", and "4") resulting from surrounding the central coverage circle 106a represented by the dot and dash border with coverage from eight adjoining emitters (four adjoining coverage circles 106b with solid borders at the four quadrants of the central coverage circle, two vertically adjoining coverage circles 106c with short dashed borders above and below the central coverage circle, and two horizontally adjoining coverage circles 106d with long dashed borders at either side of the central coverage circle). In particular the four diamond shaped portions marked "2" of the central (dot-dash) circle are each covered by the central circle and one of the horizontally or vertically oriented (dash) circles with dashed lines, the three triangular shaped portions marked "3" are each covered by the central circle, by one of the dashed circles and by one of the solid circles at the four quadrants, and the square shaped portions marked "4" are each covered by the central circle, by two dashed (one long and one short) circles, and by one solid circle.

Figure 4:
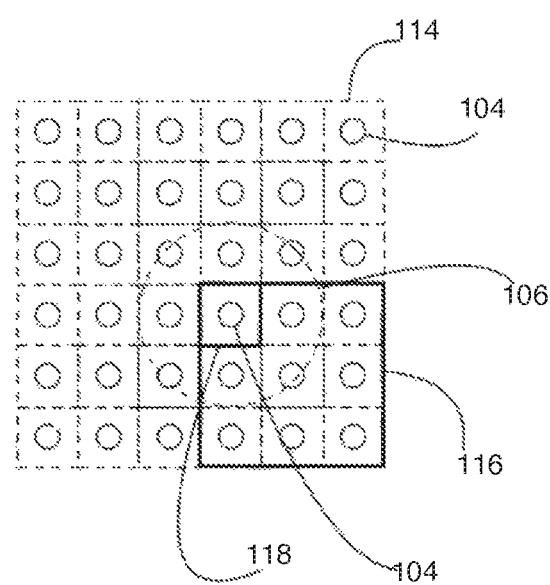
FIG. 4 shows how a 6×6 emitter array may be logically divided into four 3×3 arrays, with the coverage of a single emitter having a diameter less than the lateral dimension of one such 3×3 array.

Referring now to FIG. 4, a modular design of a two dimensional array 114 of emitters 104 with overlapping coverage areas will now be discussed, in which the emitters are operated in groups (see FIG. 5) such that there is little or no coverage overlap within the same group, but substantial coverage overlap between groups. In particular, a larger (for example 6×6) emitter array 114 may be logically subdivided divided into (or fabricated from) a number of identical subarrays (for example 3×3 arrays 116), with the coverage 106 of a single emitter 118 having a diameter less than the minimum lateral dimension of one such sub array.

As best seen in FIG. 5 (comprising 9 parts designated 5.1.A through 5.3.C) the 36 individual emitters 118 of FIG. 4 can be operated in 9 groups, each consisting of 4 emitters with corresponding coverage areas indicated with a dot surrounded by a solid circles. In particular, as shown in FIG. 5.1.A, each 3×3 subarray has been labeled along its vertical axis with numbers 1 through 3 and along its horizontal axis with letters A through C and includes 9 emitters with 9 respective coverage circles (of which, only one is active at any given time). Such a division of the array into subarrays has the useful property that a group of emitters at the same location on each subarray (for example, the top left corner) can be operated simultaneously without any overlap of their respective coverage areas. However, it should be appreciated that the coverage area from a single group of emitters may be increased without a substantial increase of overlap by using radiation patterns that more accurately reflect the geometrical relationship between adjacent emitters (for example equilateral triangles for FIG. 2 or squares for FIG. 3). Moreover, even if each emitter has a less than optimal coverage pattern (for example, the depicted circular coverage areas from respective emitters arranged in a square grid), a limited overlap may increase the useful data (i.e., measurements from only one emitter) received during a particular scan by the detectors at the corners of a particular cell at the same time it reduces the useful data received at the mid point between two adjacent emitters in the same group where the respective coverage areas overlap.

In the particular case of FIG. 5.1.A, only the emitters centered about cells 1A are active. Each emitter has a coverage area that is includes the cell in which the emitter is located and portions of the 8 cells surrounding that cell. Since emitter 1A is at the top left of each subarray, its coverage will include not only cell 1A but also cells 1B, 2B and 2A in the same subarray, cells 2C and 1C in any subarray to its immediate left, cell 3C in any subarray above and to its left, and cells 3A and 3B in any subarray immediately above. Note that the 9×9 array is modular, and accordingly, unoccupied cells on the lower row 3 and in the right column C will be in the coverage area (indicated by dotted lines) of any immediately adjacent group 1A emitters in any adjacent subarrays of that same array or an immediately adjacent array.

FIG. 5.1.C, FIG. 5.3.A and FIG. 5.3.0 are functionally similar to FIG. 5.1.A, but with the active emitters on the top right, bottom left, and bottom right corners of their respective subarrays.

In FIG. 5.1.B the coverage areas of the active emitters extend only into the subarrays (if any) immediately above. Similarly, in FIG. 5.3.B the coverage areas of the active emitters extend only into the subarrays (if any) immediately to the below.

In FIG. 5.2.A the coverage areas of the active emitters extend only into the subarrays (if any) immediately to the left. Similarly, in FIG. 5.2.0 the coverage areas of the active emitters extend only into the subarrays (if any) immediately to the right.

FIG. 5.2.B represents the simple case where the entire coverage area of each active emitter is confined within a single subarray.

Although the embodiment illustrated in FIG. 4 and FIG. 5 has only 4 subarrays each defining 9 groups, the above described modularity concept can be readily expanded, not only by increasing the size of the basic subarray (either in spacing between adjacent emitters, or in the number of emitters, or both) but also (as suggested by the dashed partial circles representing possible coverage from emitters in adjacent arrays) in all but FIG. 5.2.B) by increasing the number of arrays.

Reference should now be made to FIG. 6 (comprising FIG. 6A and FIG. 6B), which shows an alternative method for assigning the individual emitters of a single array into non-overlapping groups, based on the following procedure:

Each group is formed by selecting emitters from a predetermined "pseudo random" sequence and sequentially assigning the selected emitters to that group, subject to the constraints (1) each emitter will be assigned to only one group, and (2) no emitter will be assigned to a particular group that already includes an emitter that has a coverage area that overlaps with a previously assigned emitter.

As shown in FIG. 6A, assume the first group already includes emitters 1A, 1F, 6A, and 6F. If emitter 4A were to be selected, its coverage circle (not shown) would overlap that of previously emitter 6A. Emitters 3C, 3D, 4C and 4D are only emitters that do not have a coverage area that substantially conflicts with that of emitters 1A, 1F, 6A, and 6F. Assuming emitter 104 in cell 4D 118 is selected, it has only a slight coverage overlap 106a with emitter 6F.

FIG. 6B shows a second selection round. Assuming that emitters 1A, 1F, 4D, 6A and 6F have been selected in round one and 1B, 1E, 4A and 6C have already been selected in round 2. Then only emitters 4E, 4F and 5F are still potentially available for selection in round 2. If 4E is prior to 4F and 5F on the pseudo random sequence list, it will be chosen next. This pseudo random selection of a group of emitters with non-overlapping coverage may be repeated for another round, with 1A, 1B, 1E, 1F, 4A, 4D, 4E, 6A and 6C excluded from consideration, leaving 10, 2A, 2B, 2C, 2D, 2E, 2F, 3A,

3B, 3C, 3D, 3E, 3F, 4B, 4C, 4F, 5A, 5B, 5C, 5D, 5E and 5F available for possible selection in the third group (not shown).

Such a pseudo random selection process has the advantage that it can easily accommodate unplanned changes in availability of particular emitters or in the subsequent modifications to the device geometry. However, that flexibility comes with the added cost that a random selection process will frequently be less than optimum and that for a device having many emitters and it is not possible to test and certify in advance all possible alternatives.

Reference should now be made to FIG. 7, which is a high level functional diagram showing the flow of control signals and data within the imaging system of FIG. 1. The system is calibrated prior to use (block 120), whereby critical measurements are determined, individual emitters are sequentially operated and any defective emitters and/or detectors are identified, and system functionality is verified by producing an image of a test probe.

Assuming that the test results are within acceptable limits and any configuration changes or revised measurements have been recorded, then the system is ready for normal use (blocks 121-132). Each group of emitters is sequentially activated (block 121). The local variation in intensity of the radiation shadows projected from the individual emitters 104 onto the pixelated detector panel 102 (FIG. 1) after the group's combined radiation has passed through corresponding regions of the object 110 is measured at each individual pixel within the collective coverage area of that group (block 122) and stored (block 123). Once all the data for a particular group of emitters has been received, that data is appended to any the data already received from prior groups in store 124, and the next group of emitters is identified (block 125) and activated (block 121) and the process repeated until sufficient raw data has been captured in store 124 and transmitted (block 126) to the image processor subsystem (blocks 127, 128, 129 and 130) of the signal processing unit 108 to permit conversion of that data into the desired image of ROI 110, whereupon that data (block 130) can be converted into the desired format (block 131) and displayed (block 132) by the display subsystem 112

Certain presently preferred embodiments of an iterative image reconstruction process (blocks 127, 128 and 129) will now be discussed in sufficient detail to permit persons skilled in the computational arts to reduce to practice this aspect of the invention. With known emitter and detector locations, i.e., the known positions of each energized emitter 104 and of the pixels within the detector panel 102 at which corresponding radiation rays are received, the shadow data collected by the respective detector during each scan represents how much radiation (if any) transmitted from each emitter reached each pixel in the detector array. In broad terms, the space or object to be imaged is subdivided into three-dimensional non-overlapping volume elements, referred to as voxels and the process of defining (or redefining) those voxels may be referred to as voxelization (or re-voxelization). The linear attenuation coefficient of the part of the object 110 occupying each voxel will typically vary from voxel to voxel, and a data vector corresponding to these attenuation coefficients is determined (i.e., each voxel is modeled as being occupied by part of the object consisting of homogeneous material whose attenuation coefficient represents a single sample, or data point, and all of these data points are collected in an array called a vector).

By way of example, for 10 and 50 keV X-rays, and considering a human body, the values of the linear attenuation coefficient x are approximately as follows:

TABLE 1

Attenuation coefficients for different tissue types.

| Material | at 10 keV | at 50 keV |
| --- | --- | --- |
| Adipose tissue | $x = -3.11$ cm$^{-2}$ | $x = -0.20$ cm$^{-2}$ |
| Water | $x = -5.33$ cm$^{-2}$ | $x = -0.23$ cm$^{-2}$ |
| Muscle | $x = -5.63$ cm$^{-2}$ | $x = -0.24$ cm$^{-2}$ |
| Bone | $x = -54.72$ cm$^{-2}$ | $x = -0.81$ cm$^{-2}$ |

Thus, bone produces considerably more attenuation than the other listed body components (in the absence of any contrast media), and the attenuation coefficient depends not only on the material, but also on the energy (i.e., the frequency) of the X-rays.

Even with more detectors (pixels) than emitters and with sequential operation of the individual emitters (or predetermined sets of emitters) with non-overlapping radiation cones projected onto the detectors, in medical imaging applications involving a living patient there are practical constraints for the total radiation exposure and elapsed time required for the procedure which will limit the amount of data received from all possible emitter/detector pairings. As a result there will not in general be sufficient data to unambiguously transform the information received from the detector panel into the corresponding attenuation value of each voxel of a reconstructed 3D image having resolution comparable to that of the 2D detector array (in mathematical terms, the data is under-constrained). Accordingly, compressed sensing methodology (preferably but not necessarily limited to computationally efficient basis pursuit algorithms) is employed to determine a set of attenuation coefficient values which best fit the available data (and reduce a merit function to a minimum).

The imaging domain is preferably voxelized via a hierarchical subdivision, which may generally correspond to (or may easily be transformed into) the physical alignment and spacing of the emitters and the detectors and the object space located therebetween. An optimal voxelization is obtained by iteratively (branch 129 from block 128) amending the voxelization (block 127) until a quantitative stopping criterion is satisfied, such as exceeding a fixed number of iterations or satisfying predetermined optimality conditions within a specified tolerance. Each successive change of voxelization is henceforth referred to as an outer iteration. Within each outer iteration, the voxelization is kept fixed and a compressed sensing optimization model is set up (block 128), as further discussed below, the solution of which determines the attenuation coefficients associated with each voxel of the current voxelization. The compressed sensing process used to obtain the attenuation coefficients for a particular outer optimization will typically also involve an iterative method (specific choices being discussed below) with the compressed sensing steps within each particular voxelation outer iteration henceforth referred to as an inner iteration.

When a hierarchical subdivision is used, an initial voxelization (block 127 from block 126) is chosen. In particular, the entire imaging domain may be used as a single initial voxel, or the initial voxelization may be obtained from a regular grid or from a subdivision of the imaging domain into simplices or more general polyhedra or polytopes. In subsequent outer iterations (block 127 via branch 129) each voxel (called a parent voxel) of the previous voxelization (in the first outer iteration, the initial voxelization plays the role of previous voxelization) may be further subdivided into two or more smaller voxels (called child voxels). For example, if a parent voxel is to be subdivided into two child voxels, a single cutting hyperplane may be introduced, and if a parent voxel is to be subdivided into four child voxels, two mutually perpendicular such cutting hyperplanes may be used. The subdivision process may then be applied recursively, with child voxels taking on the role of parent voxels that are subdivided further, into their own child voxels.

An opposite operation can be carried out as well, that is, the local (or global) coarsening of a voxelization. This consists of merging two or more adjacent voxels that occupy a convex polyhedral domain into a single super-voxel that occupies this domain. For voxelization that were obtained by hierarchical subdivision, this may simply involve identifying the super-voxel among the parent voxels and cutting off its children, thus turning the particular parent voxel into a leaf of the data structure tree. If no parent voxel corresponds exactly to the domain of the supervoxel, a parent voxel that contains the super-voxel has to be identified and subdivided so that one of the new leaves corresponds to the super-voxel. When an explicit addressing system is used, the merger of voxels can be achieved by overwriting either inserting or appending a data structure associated with the super-voxel to the list of addresses of the existing voxelization and deleting the addresses of the data structures associated with the voxels that are to be merged. In another implementation, instead of explicitly merging sets of voxels into supervoxels, constraints are introduced that force the attenuation coefficients of all individual voxels belonging to a single voxel superset (that is, the totality of voxels that would be merged into a single supervoxel) to take the same value, which represents the attenuation coefficient of the supervoxel that would have resulted from the merger of this set of voxels. Thus, the merging operation may be carried out implicitly instead of explicitly, with each of the supersets corresponding to a different constraint.

In order to perform the numerical reconstruction of the attenuation coefficients associated with all of the voxels, a data structure is required that associates a voxel with its position in space, with the value of its attenuation coefficient, and with possibly other data that help relating the voxel to its neighbors and facilitate the operations of local refinement and coarsening further described below. For voxelizations associated with a regular grid, an explicit addressing system may be used, based on vectorizing the grid. In a hierarchical subdivision of voxels, an implicit addressing system can be used: Starting with an addressing system of the initial voxelization, a rooted tree structure may be appended at each voxel of the initial voxelization, with each of the initial voxels at the root of its tree, the first level of the tree corresponding to its children, the second layer corresponding to their grand children etc. The individual leaves of the tree thus will correspond to the voxels in the final voxelization which collectively (the set union of all the leaves on that tree) correspond to the original voxel at the root of the tree. Information or data can be sent to the data structure associated with each voxel of the final voxelization by sending it to the root of the tree in which they are located (using the addressing system of the initial voxelization), and by designing the data structure associated with each parent voxel in the tree to pass the data on to its child voxels, applying this process recursively. Data or information can be extracted from the data structures associated with the voxels of the final voxelization by passing the data to the data structure associated with their parent, by applying this process recursively so as to pass the data up to the root voxel associated with the tree in which the voxel initiating the data communication is located, and by extracting the data from the root voxel by use of the addressing system used for the initial voxelization. A third approach is to use a hybrid addressing system when the initial regular grid is sometimes locally coarsened into a regular grid with a larger grid size. In this case, the regularity of the refined local grid may be used to arrive at an explicit addressing system for the overall voxelization, by inserting or appending the addresses of the remaining (coarsened) original voxels into the corresponding list of the new addresses associated with the coarser grid which has replaced the original address list.

The attenuation of a ray of X-rays within a particular voxel is dependent on the attenuation coefficient x determined by the material occupying the voxel (which is assumed to be homogeneous over the space associated with the voxel) and the energy at which the X-ray beam is emitted. Henceforth, the attenuation coefficient of the i-th voxel is labelled as $x_i$.

The second factor determining attenuation of the ray while traversing a voxel is the distance travelled by the ray through the voxel; for the i-th voxel, this distance will be denoted by $\xi_i$. By the well known Beer-Lambert Law, the proportion of photons entering the voxel that are not absorbed during the traversal of voxel i is given by $\exp(x_i\xi_i)$. This formula is still true when a ray does not traverse voxel i at all, as in this case we have $\xi_i=0$ and $\exp(x_i\xi_i)=1$, corresponding to no absorption at all. In all cases we have $0<\exp(x_i\xi_i)=1$, since $x_i$ is either zero or negative, and $\xi_i$ is either zero or positive. The attenuation of a ray of photons that traverses multiple voxels accumulates multiplicatively, so that the relationship between the intensity $I_E$ of the ray at emission and the intensity $I_D$ of the ray at a detector (where the remaining radiation is measured and absorbed) is given by $$I_D = I_E \times \exp(x_1\xi_1 + x_2\xi_2 + \ldots + x_n\xi_n), \quad (1)$$

where n is the total number of voxels. A linear equation can be obtained by taking logarithms:

$$\log(I_D/I_E) = x_1\xi_1 + x_2\xi_2 + \ldots + x_n\xi_n. \quad (2)$$

Any voxel that is not intersected by the ray will have a distance value of $\xi_i=0$, and thus the corresponding variable $x_i$ is effectively eliminated from the equation. The set of rays measured will each produce an equation of this form and so a system of these linear equations can be represented in a matrix A of size m×n, in association with a corresponding vector b, where m, the number of rays, may be much less than n (the number of voxels), perhaps by a factor of 10 or more. In an exemplary model, each ray corresponds to an emitter-detector pair, as we model the photons that are emitted at an emitter 104 and a detector on the detector panel 102 as traversing the object 110 along a line (which we refer to as the ray). This is a model assumption, since in practice these photons traverse the object in a narrow cone that approaches a line as the size of the detectors approach zero, and some photons are also scattered outside this cone. The ray that corresponds to an emitter-detector pair is defined by the line segment between the centers of the emitter and detector, to which the narrow cone is collapsed under our model assumption. For example, if the detector panel contains on the order of $10^6$ detectors and the emitter panel on the order of $10^2$ emitters, then the number m of rays is on the order of $10^8$, while the number n of voxels might be chosen on the order of $10^9$, in order to achieve the same 3D resolution as the 2D resolution offered by the detector panel. The calculation of the distances $\xi_i$ is made possible by the fact that the relative position of the emitter e and detector d is known, as is the position of voxel i relative to these points once the voxelization is fixed.

The matrix A and vector b described here can immediately be used in a basis pursuit problem without any further alterations. A major advantage of this model is that the matrix A is constructed after the attenuation measurements have been obtained. This allows one to choose different voxelizations for the same set of measurements and, therefore, a process of trial and error can be used to improve the voxelization so as to result in the best quality image fit for the intended purpose. To construct the matrix A, the distances have to be computed for every ray (corresponding to an emitter-detector pair) and every voxel the ray traverses along a section of positive length. All other coefficients of the matrix are zero.

A simple method to determine the nonzero coefficients of the matrix A is to use ray tracing, in which the entry and exit points of the ray in a traversed voxel are computed, and the exit point is identified as the entry point of the next voxel the ray traverses. This method has a natural parallelization. It can be further accelerated in the case where the voxelization derives from a regular grid, by exploiting the fact that in voxels whose entry and exit points are located at opposing parallel faces, the two points are offset by the same constant vector (which depends on the direction of the ray and the orientation of the two faces). The nonzero coefficients of matrix A can then be computed from the length of the intersection of each ray with each voxel of the initial voxelization, and then the length of the intersections with each voxel in each of the rooted trees may be determined recursively by subdividing the intersection of the ray with each parent voxel into line segments corresponding to the intersection of the ray with the children voxels of the parent. For example, if each parent voxel is split into two child voxels by a cutting hyperplane, then the point of the line segment associated with the parent that separates the line segments associated with the child voxels is given by the intersection of the ray with the hyperplane. If the intersection point lies outside the parent voxel, only one of the two child voxels has a nonzero intersection with the ray, the length of which is identical to the length of the line section associated with the parent. This iterative process also has a natural parallelization.

Using this matrix terminology, the equation to be solved is of the form:

$$Ax=b, \quad (3)$$

where x is a n-component vector representing each of the different values $x_i$, b is a m-component vector representing the measured intensities $I_D$ (after absorption) for each different ray, and A is a m×n matrix with one row corresponding to each ray, this row consisting of the distances $\xi_i$, (i=1, . . . , n) of the intersections between the ray and each voxel.

In addition to the system of equations, further constraints may be imposed on the decision vector x. These take the form $$Bx=v,$$

$$Cx \leq b, \quad (4)$$

where B and C are $m_B \times n$ and $m_C \times n$ matrices with real coefficients, and v, z are real vectors of size $m_B$ and $m_C$ respectively, and where the equality and inequality signs must hold componentwise for the vectors on both sides of the equations or inequalities. The number $m_B$ of equality constraints may be zero, but there are always at least $m_C \geq n$ inequality constraints corresponding to the non-positivity conditions $x_i \leq 0$, (i=1, . . . , n). Other constraints may include upper and lower bounds on specific coefficients of x, $$l_i \leq x_i \leq u_i, \quad (5)$$

which may for example be derived from a reconstruction of x via a different model or algorithm, or from a priori knowledge derived from a set of priors, or equality and inequality constraints on a subset of coefficients of x derived from a reconstruction on a different voxelization, for example, $$x_i = x_l \quad (6)$$

when one wishes to model the voxels i and l as merged without introducing a data structure for the merged supervoxel, its attenuation coefficient corresponding to the common value of $x_i$ and $x_l$.

More generally, one should also take into account the fact that there may be noise or errors in the observations. Thus, consider a system of equations and inequalities:

$$Ax=b+\varepsilon,$$

$$Bx=v,$$

$$Cx \leq z, \quad (7)$$

where A, x and b are as described above, and E is a vector of noises, the j-th component $\varepsilon_j$ corresponding to the measurement noise of the j-th ray, given by an emitter-detector pair (e, d). In this setup, the term $b_j$ represents the measured intensity of ray j at detector d, while $b_j + \varepsilon_j$ represent an (unobservable) ground truth measurement that would be obtained under idealized conditions, while the noise term $\varepsilon_j$ captures the aggregate difference between the two values due to many separate sources of inaccuracies:

i. The emission intensity of X-rays emitted at emitter e in the direction of detector d may deviate from the assumed value $I_E$, as a result of defects, material deterioration, deviations from the design geometry, energy supply and random effects within the emitter, or parts of the emitter panel connected to the emitter.

ii. As already mentioned, photons are transmitted from emitter e to detector d within a section of space described a narrow cone, while the ground-truth measurement $b_j$ posits collapsing this angle space to a line segment that connects the centers of emitter e and detector d. As a result, different photons traverse a particular voxel along line segments of slightly differing lengths, which causes the number of photons arriving at detector d to be slightly different from the theoretical value implied by $b_j$.

iii. While traversing the object from emitter e to detector d, a random number of photons are scattered and change directions in a random fashion, arriving and being detected at a detector different from d. This causes the number of photons detected at d that have been emitted at e to be smaller than the theoretical value. At the same time, a random number of photons being transmitted along other rays are scattered, some of which arrive and are detected at detector d, with the effect of increasing the detection count over its theoretical value. The two phenomena occur conjointly, which can cause the actual number of photons to be detected at detector d to be either smaller or larger than the theoretical value, the actual deviation being random.

iv. The detection of photons at detector d is itself based on a physical process that involves Poisson thinning, causing a random number of arriving photons to remain undetected. One can correct for the expected error by appropriately scaling up the actual measurement, but the resulting measurement is still random. Impurities, deterioration, and material and geometric defects within the detector d, as well as variations within the parts of the detector panel connected to detector d, the wireless, wired or fiber optic connection of the detector panel to data storage or computer hardware, as well as variations within that hardware itself all add further noise to final value of the stored measurement of the intensity of X-rays transmitted along ray j that will be used in the image reconstruction computation.

Note that the constraints in the last two relationships of (7) for Bx and Cx do not contain any noise, as these are hard constraints imposed by the modeler or by laws of physics.

The system of linear equations Ax=b may be underdetermined (corresponding to the case m<n), invertible (corresponding to m=n and A nonsingular), or overdetermined (corresponding to m>n), depending on the resolution of the chosen voxelization. Finer voxelizations result in more under-determined systems. Correspondingly, when an image with fine resolution is required, the system is typically under-determined, for example by a factor 10 or more.

The solution to such an under-determined system of equations may be solved by techniques known as basis pursuit. This uses techniques studied in the field of compressed sensing. Compressed sensing is concerned with the acquisition of data and its recovery in a system that is under-determined. The technique exploits a key feature that is common amongst many such signals, namely that they often have a sparse representation in some basis. This additional property allows us to impose an extra condition on the problem of recovering the solution vector: it should have as few non-zero entries as possible. As explained above, an X-ray image is particularly used to investigate areas of higher density and higher attenuation coefficient, such as bones or particular organs infused with an appropriate contrast medium, which occupy a relatively small proportion of a body's volume. In medical imaging applications, it is therefore reasonable to expect that a signal arising from such an image will be sparse with regard to values of attenuation coefficient. The density gradient field of most objects is also sparse, due to sharp interfaces between materials of high and low attenuation. Mathematically this type of sparsity can be exploited in much the same way as sparsity in the vector x itself.

Allowing for the presence of errors, the system of equation to be solved, expressed as a basis pursuit is the following, $$\min_{x \in \mathbb{R}^n} \quad \|x\|_1, \qquad (8)$$
$$\text{subject to} \quad Ax = b + \varepsilon,$$
$$Bx = v,$$
$$Cx \leq z,$$

where $\|x\|_1 = \sum_{i=1}^{n} |x_i|$ is the 1-norm of the vector x of decision variables $x_i$. Due to the non-positivity constraints $x_i \leq 0$, incorporated among the constraints $Cx \leq z$, we have $\|x\|_1 = -\sum_{i=1}^{n} x_i$, so that finding the optimal decisions x for the above problem is readily achieved by solving the linear programming problem $$\max_{x \in \mathbb{R}^n} \quad \sum_{i=1}^{n} x_i, \qquad (9)$$

subject to $Ax = b + \varepsilon,$ $Bx = v,$ $Cx \leq z.$

This is not the only way to reformulate the above problem in linear programming form. In fact, there exist infinitely many reformulations, for example, $$\min_{(x,y) \in \mathbb{R}^{2n}} \quad \sum_{i=1}^{n} y_i, \qquad (10)$$
$$\text{subject to} \quad Ax = b + \varepsilon,$$
$$Bx = v,$$
$$Cx \leq z, \quad y_i - x_i \geq 0, (i = 1, \ldots, n)$$
$$y_i + x_i \geq 0, \qquad (i = 1, \ldots, n)$$

The noise term $\varepsilon$ in problem (7) can be treated in several different ways:

i. Treating $\varepsilon$ as known (e.g., $\varepsilon=0$) yields the linear programming problem $$\max_{x \in \mathbb{R}^n} \quad \sum_{i=1}^{n} x_i, \qquad (11)$$
$$\text{subject to} \quad Ax = b,$$
$$Bx = v,$$
$$Cx \leq z.$$

In this form the problem can be solved by any of the known LP algorithms, including the following non-exhaustive list: the simplex algorithm, interior point algorithms, subgradient algorithms, the ellipsoid method, bundle methods, the perceptron algorithm, Bregman-projection algorithms, Nesterov's smoothing algorithm, randomized coordinate descent methods, and variants of alternating block coordinate descent algorithms. The latter are particularly well suited to solving large scale problems of the form (3), which are LPs with special structure.

ii. Treating the noise as unknown, a regularization term $\Phi(\varepsilon)$ can be added into the objective function, $$\max_{(x,\varepsilon) \in \mathbb{R}^{n+m}} \quad \sum_{i=1}^{n} x_i - \Phi(\varepsilon), \qquad (12)$$
$$\text{subject to} \quad Ax = b + \varepsilon,$$
$$Bx = v,$$
$$Cx \leq z,$$

where $\Phi(\varepsilon)$ is a convex (and typically, non-negative) risk function of the noise vector $\varepsilon$. This changes the objective to finding a decision vector x that approximately satisfies the system of equations Ax=b, and where the term $\Phi(\varepsilon)$ gives an incentive to keep the residual $\varepsilon=Ax-b$, that is, the deviation of the implied measurements b from the ground-truth measurements b+$\varepsilon$, small. Popular choices of the regularization term include the following:

$\Phi(\varepsilon) = \lambda \|\varepsilon\|_1$, with $\lambda > 0$. In this case, the problem can be formulated in linear programming form, $$\max_{(x,\varepsilon,t) \in \mathbb{R}^{n+m+m}} \sum_{i=1}^{n} x_i - \lambda \sum_{j=1}^{m} t_j, \quad (13)$$

subject to $\quad Ax = b + \varepsilon,$ $\quad Bx = v,$ $\quad Cx \le z, \quad t_j \ge \varepsilon_j, (j = 1, \ldots, m),$ $\quad t_j \ge -\varepsilon_j, \quad (j = 1, \ldots, m).$ The algorithmic approaches discussed in i) can also be used to solve the resulting problem.

$\Phi(\varepsilon) = \lambda \|\varepsilon\|_2^2 := \lambda \sum_{j=1}^{m} \varepsilon_j^2$, with $\lambda > 0$. This least-squares approach can either be interpreted as a constrained regression aimed at minimizing the variance of the noise term, or as a constrained maximum-likelihood estimation of x under the assumption that the noise is Gaussian. The resulting problem $$\max_{(x,\varepsilon) \in \mathbb{R}^{n+m}} \sum_{i=1}^{n} x_i - \lambda \|Ax - b\|_2^2, \quad (14)$$

subject to $\quad Bx = v,$ $\quad Cx \le z$ is a convex quadratic programming problem that can be solved, among other algorithms, by an SOCP solver, the active set method, subgradient, bundle and ellipsoid methods, and by alternating projection.

$\Phi(\varepsilon)$ can be chosen as a norm or the square of a norm designed to specifically model structure and sparsity in the noise term. Examples of such norms can model the noise of measurements at nearby detectors being correlated, or that noise occurs only in sparse detector locations, or at sparse contiguous blocks of detectors, or that the noise arises due to physical damage in a sparse set of emitters, or an overlay of several of these approaches. Variants of subgradient methods, bundle methods, Bregman projection, block-coordinate descent and interior-point methods can be used to solve such problems, as well as algorithms for general nonlinear optimization, such as sequential quadratic programming, interior point methods, quasi-Newton methods, the proximal method, the augmented Lagrangian method, trust region methods and many more.

iii. Instead of building the error into a merit function, maximum allowances for the error can be formulated as inequality constraints. This involves specifying a budget of constraint violation:

$$|\varepsilon| = |Ax - b| \le u, \quad (15)$$

where u is a vector of size m with strictly positive coefficients. The resulting problem is $$\max_{x \in \mathbb{R}^n} \sum_{i=1}^{n} x_i, \quad (16)$$

subject to $\quad |Ax - b| \le u,$ $\quad Bx = v,$ $\quad Cx \le z,$ where $|Ax - b|$ denotes the vector of componentwise absolute values of the vector $|Ax - b|$. This problem can again be formulated in LP form and solved via any of the techniques listed in i).

iv. More generally, a budget on a nonlinear function $ of the constraint violation may be set, to arrive at a problem of the form $$\max_{x \in \mathbb{R}^n} \sum_{i=1}^{n} x_i, \quad (17)$$

subject to $\quad \Phi(Ax - b) \le u,$ $\quad Bx = v,$ $\quad Cx \le z,$ with $\Phi(\varepsilon)$ taking any of the forms discussed in ii). Any of the algorithmic approaches discussed there can be applied.

The development of algorithms to solve $l_1$ minimization problems has been the subject of much study in compressed sensing literature and there exist a variety of methods for this purpose. For the purposes of specificity, we use the YALL1 algorithm ("Your Algorithms for $l_1$") developed by Y. Zhang, J. Yang, and W. Yin at Rice University, an algorithm that solves many variations of the $l_1$ problem and thus yields a flexible tool for prototyping. YALL1 is based on based on the alternating direction method of multipliers, see J. Yang and Y. Zhang: Alternating Direction Algorithms for $l_1$ problems in Compressed Sensing, SIAM Journal on Scientific Computing, vol. 33 no. 1, pages 250-278, 2011, and also available at http://www.caam.rice.edu/zhang/reports/tr0937.pdf.

For further specificity, we henceforth concentrate on the $l_1$ problem, although any known models for accounting for measurement error can be used in conjunction with the invention, amongst which the pure $l_1$ problem is not the most preferred. Therefore, none of what follows in the discussion below is restricted to the $l_1$ problem. It is easily seen that problem (13) converges to the basis pursuit problem (11) in the limit as A tends to zero. For any non-zero $\lambda$, (13) offers a relaxation of (11) in the sense that the equality constraints arising from the measurements need not be satisfied exactly, but instead any violation of the constraints are penalized. In fact, it is not desirable to set A to zero, both because measurement errors are an inevitable fact, and because the ground truth of decision vector x, i.e., the actual density vector of the imaged object, is not actually sparse but instead contains a sparse set of coefficients that are much larger in absolute value than the majority of coefficients. A nonzero $\lambda$ allows for coefficients that are small in magnitude to be effectively rounded to zero by the deployment of a sparsity-inducing model.

Referring again to FIG. 1 and FIG. 7, for any given voxelization, the design matrix A can be computed as discussed above: In a series of temporally separated exposures, groups of emitters on the emitter panel 104 are selected and activated (blocks 121 and 125 of FIG. 7) in such a way (eg, as shown in FIG. 3 through FIG. 5) that the multiple cones of X-ray xxradiation produced by any one such group pass through the object 110 and, assuming idealized conditions in which no scattering takes place, arrive on the detector panel 102 in substantially non-overlapping fashion. That is, under idealized conditions, any photons that arrive at an active detector on the panel 102 during the measuring process of a single exposure are emitted by a single emitter. By taking several exposures separated in time and varying the groups of emitters that are activated simultaneously in each particular exposure, any particular detector (pixel) on the detector panel 102 successively measures X-rays arriving from different emitters, thus allowing spatial overlap in measurements that are temporally separated.

During each exposure, for example as shown in the multiple views of FIG. 5, a different set of emitters, arranged in an emission pattern, is activated. If the emission pattern of a particular exposure is arranged so that X-rays are emitted from emitter e on the emitter panel 104 in the direction of detector d on the detector panel 102, we say that the emitter-detector pair (e, d) is activated. Any emitter-detector pair j=(e, d) that is activated in one of the several temporally separated exposures defines an emission ray j, and correspondingly, a row j of matrix A, whose coefficient $\xi_{j,i}$ is given by the length of the line segment determined by the intersection of ray j with voxel i, where the column indices i are enumerated in the same order (implicit or explicit) as the voxels in the chosen voxelization. The lengths $\xi_{j,i}$ are computed as discussed above, and the geometry of the emitter panel 104, its position relative to the detector panel 102 and the sets of emitters that are activated in successive temporally separated exposures are chosen such that at least one emitter-detector pair j=(e, d) for which $\xi_{j,i} \neq 0$ is activated in the course of some exposure or another for each voxel i for which a reconstruction of the attenuation coefficient $x_i$ is desired.

When the voxels are enumerated implicitly via the tree structure discussed earlier, or via a set of such trees when the initial voxelization has an explicit enumeration, the coefficients $\xi_{j,i}$ may be held in the data structure that corresponds to the leaves of the tree (or trees), rather than assembling the matrix A explicitly. This may be advantageous when the chosen voxelization is very fine grained and thus contains a large number of voxels. In this case, each parent voxel of two (or more) child voxels is also associated with a data structure that may store the length of the intersection of ray j with its associated (parent) voxel, which corresponds to the sum of the coefficients $\xi_{j,i}$ associated with the children i. In this manner, the coefficients of the design matrices corresponding to a nested hierarchy of successively refined voxelizations is stored in computer memory or on a data carrier and addressed implicitly.

The column vector b is composed of components $b_j$, one for each ray that corresponds to an emitter-detector pair (e, d) that is activated in any of the several temporally separated exposures. The coefficient $b_j$ is computed as $b_j = \log(I_D/I_E)'$ where log is the natural logarithm, $I_E$ is the intensity at which emitter e on the emitter panel 104 emits X-rays in the direction of the detector d on the detector panel 102 and $I_D$ is the intensity at which X-rays arrive at the detector d, measured by detector d during the exposure when the pair (e, d) is activated.

Once the matrix A and the vector b are assembled, the YALL1 algorithm, can be used to solve the associated problem, $$\max_{(x,\varepsilon) \in \mathbb{R}^{n+m}} \sum_{i=1}^{n} x_i - \lambda \|Ax - b\|_2^2, \qquad (18)$$

subject to $\quad Bx = v,$ $\qquad\qquad\quad Cx \leq z,$ or any other of the above discussed models. The resulting vector x yields a data representation of the reconstructed image of the object, the i-th component $x_i$ corresponding to the numerically reconstructed attenuation coefficient associated with voxel i under the model assumption that voxel i is occupied by homogeneous material. The values $x_i$ may be used either to produce a graphical representation of the objector part thereof, either in 3D, or in 2D or 1D slices, or of 2D projections in any chosen projection direction, or it may be used to simulate a classical parallel shadowgraph of the object, or it may be used to automatically detect certain features of interest, such as spatial areas within the object where specific materials or anomalies or defects are present, or to compute the geometry of a specific part within the object, for example a particular bone or part thereof, or the shape of an organ or blood vessel, with the aim of using this geometric data for the production of medical implants or for medical diagnosis, such as pathology, trauma, objects lodged in tissue etc. In security applications, it may be used for the automatic detection undesired or dangerous objects. In destruction-free quality control it may be used to automatically detect material defects, such as cracks or the inclusion of air pockets or excess material in 3D printing or casting applications.

If a voxelization with implicit enumeration is used, all linear algebra operations required in the course of running the algorithm to solve the problem may be applied hierarchically as well, using the same nested hierarchy of voxelizations and the associated data structures. In particular, this applies to matrix-vector products, Gaussian Elimination, the identification of pivots, and the application of Givens Rotations or Householder Reflections. Correspondingly, the vector x also has a nested hierarchical representation that corresponds to the nested hierarchical voxelization, and component i may be stored in the data structure associated with voxel i, rather than assembling the vector x explicitly. For example, if a parent voxel k is subdivided into two child voxels i and l, each of the data structures associated with these voxels stores a value $x_k$, $x_i$ and $x_e$ respectively of the final value that vector x takes after completion of the algorithm (which may be and typically is iterative in nature), with $x_i$ corresponding to the numerically reconstructed attenuation coefficient of the hypothesised homogeneous material occupying voxel i and $x_l$ corresponding to the numerically reconstructed attenuation coefficient of the hypothesized homogeneous material occupying voxel e. Likewise, $x_k$ corresponds to the numerically reconstructed attenuation coefficient of the hypothesised homogeneous material occupying voxel k, but seen as this is the parent voxel consisting of the union of child voxels i and k, the model assumption of homogeity of voxel k is generally inconsistent with the model assumption of homogeneity of voxels i and l, as in the finer voxelization the attenuation coefficients $x_i$ and $x_l$ are allowed to take different values, while in the coarser voxelization of which the parent voxel k is a voxel, the material that occupies both voxels i and l is forced to take the same attenuation coefficient. For this reason, $x_k$ will generally lie in between $x_i$ and $x_l$, at a value close but not equal to the weighted average $$x_k \approx \frac{\xi_{j,i}}{\xi_{j,i}+\xi_{j,\ell}} x_i + \frac{\xi_{j,\ell}}{\xi_{j,i}+\zeta_{j,\ell}} x_\ell \qquad (19)$$

of $x_i$ and $x_\ell$, with weights proportional to the intersection lengths $\xi_{j,i}$ and $\xi_{j,\ell}$ of a ray j that intersects both child voxels. Note that this average depends on the ray j chosen, but seen as the attenuation coefficients of nearby voxels are almost equal in most places for fine enough voxelization, the difference is minor.

In iteratively refining versions of the algorithm, the value $x_k$ can be computed first, as it is computationally cheaper to solve problem (13) for a coarser voxelization, and $$x_i^{[0]}=x_k, x_\ell^{[0]}=x_k \qquad (20)$$

can then be used as starting values for an iterative algorithm to solve problem (13) on the finer voxelization. The same initialization may also be used when the voxelization is refined in the course of an outer iteration, which will be described below, each of which consists of solving an instantiation of problem (13) on a fixed voxelization, followed by a set of calculations that locally refines and/or coarsens the voxelization depending on quantitative criteria that shall be described below. The new voxelization is used to set up the instantiation of problem (13) used in the next outer iteration. This process is repeated until a termination criterion is satisfied, for
example, when the voxelization is no longer amended or after a fixed number of outer iterations have been carried out.

When the voxelization is addressed via an explicit addressing system, such as when a regular grid is used, an similar initialization may be used in which the initial value of the attenuation coefficient of the refined voxels equal the numerically computed value of the attenuation coefficient of the voxel from which they are refined.

Similarly, if in the course of an outer iteration the voxelization is locally coarsened, the attenuation of a new super-voxel may be initialized via weighted averaging of the attenuation coefficients of the constituent voxels, with relative weights proportional to the intersection lengths of a ray that traverses all of the constituent voxels. In particular, if the merged voxels are the child voxels of a parent voxel in a hierarchical voxelization, then this averaging formula approximately equals the weighted average $$x_k \approx \frac{\xi_{j,i}}{\xi_{j,i}+\xi_{j,\ell}} x_i + \frac{\xi_{j,\ell}}{\xi_{j,i}+\xi_{j,\ell}} x_\ell. \qquad (21)$$

Note that this initialization depends on the ray chosen, but seen as the values do not differ significantly in most places when a different ray is chosen and in view of the fact that the averaged value yields just the starting points for an globally convergent iterative optimization algorithm for a convex problem, this issue poses no difficulty. An appropriate ray always exists, as each voxel is traversed by at least one ray, and intersection lengths $\xi_{i,j}=0$ are allowed for some (but not all) terms that appear in the averaging formula.

The first outer iteration may start with the assumption that no prior information is known about the object that is to be imaged. In this case, a regular grid may be used as initial voxelization, or any other voxelization of choice. The size of voxels may be chosen an order or two larger than the resolution that is desired for the final reconstructed image, as this will speed up the computation time of the first outer iteration. Another approach is to use prior information to set up the initial voxelization. Prior information may be available in the form of the optimal (final) voxelization of an image of a similar object that was previously reconstructed. For example, in a medical context where a chest X-ray is taken, the optimal voxelization of a chest X-ray taken of a previous patient may be used as initial voxelization. If the imaged object is a skull, a prior voxelization of a skull may be used etc. Several prior voxelizations of similar objects may be kept in a library from which the best fitting is chosen. For example, among the prior voxelizations of a library of skull images, the proportions of length to width and height may be compared with the current patient, and the prior with ratios most closely matching the current patient may be chosen and appropriately scaled. The selection of prior from a library may be based on other quantitative criteria, or the choice may be made by a human subject matter expert, for example, a clinician in a medical context, an airport security expert in an airport security screening context, a border control agent in the context of vehicle screening and so forth. A third approach to choosing an initial voxelization is to place a model object in between the emitter and detector panels, to expose the model object to temporally sequential X-ray exposures, to start with no prior or an educated guess of a prior voxelization for the model object in a first outer iteration of the image reconstruction method for the model, to iteratively amend the voxelization associated with the image reconstruction of the model object in each outer iteration of the model object image reconstruction process, and to take the final (optimal) voxelization of the model object as the initial voxelization of the actual object that is to be imaged. This method may be employed in order to establish a library of priors, or it may be used on an ad hoc basis, by choosing as model object an object whose 3D content and the geometry thereof can be assumed to be similar to that of the object that one wishes to image.

Once an initial voxelization has been chosen, the design matrix A can be established as discussed earlier and kept in computer memory or on a storage device, either in explicit or implicit form. The last two constraints of (7) are set up as required, by generating the relevant matrices and vectors and storing them on a computer or storage device. Once the problem data has been assembled, the corresponding instance of problem (13) (or any other of the above discussed models) may be solved via one of the previously mentioned algorithmic approaches. Most of these algorithms are iterative in nature, that is, they take an initial or existing (suboptimal) decision vector $x^{[k]}$ (where k=0 for the initial decision vector and k=1, 2, 3, . . . in subsequent iterations) and use this information to find an improved solution $x^{[k+1]}$, in the sense that the objective or merit function of the optimization problem (13) takes a better value, in our case a larger value, as problem (13) is formulated in maximization form. This optimization process for a given voxelization process is applied iteratively, and each such iteration is referred to as an inner iteration.

In contrast, an outer iteration consists of selecting, computing, looking up or being communicated a voxelization, assembling the matrices A, B, C and vectors b, v, z associated with this voxelization, iteratively solving the problem instance of Model (13) determined by these problem data, and finally, using the reconstructed optimal decision vector x to decide on the voxelization to be used in the next outer iteration, as well as the initial starting point $x^{[0]}$ of the next outer iteration. Alternatively, the optimal vector x may be communicated to the next outer iteration, and outer iterations may be designed to use this information in computing their associated voxelization and initial solution $x^{[0]}$ at the start of the iteration rather than at the end. Thus, each outer iteration of the reconstruction method comprises a plurality of inner iterations as part of the computations associated with it.

The optimal decision vector x resulting from the optimization problem (13) associated with an outer iteration may be used to amend the voxelization associated with this iteration to a voxelization to be used in the next outer iteration, as well as to compute an initial solution $x^{[0]}$ to be used to start up the inner iterative process in the next outer iteration. The main mechanisms were already explained above: the voxelization is amended by local refinement and coarsening, and the initial values of $x^{[0]}$ corresponding to new voxels are primed using the formula (3) in the case of refined voxels, and by an analogue of formula (2) in the case of super-voxels resulting from merging voxels in local coarsening. For all other voxels i, $x_i^{[0]}$ may equal $x_i$, that is, the corresponding coefficient of the optimal decision vector of the previous outer iteration is used as the starting value of the coefficient associated with the same voxel in the next outer iteration. Using this process guarantees that the numerical computation carried out in the next outer iteration is computationally less costly, as it is mainly the values of x associated with new voxels that change, while the coefficients associated with other voxels are merely fine tuned, a process that is usually achieved after only a few inner iterations.

It remains to describe how, as a function of the optimal decision vector x of the previous outer iteration, voxels that shall be refined or coarsened are selected. A first mechanism to amend the voxelization, one by which areas of local coarsening may be determined, is to search the vector x, making use of the spatial adjacency information about voxels, to identify voxels i whose associated attenuation coefficient $x_i$ has high absolute value and are surrounded by voxels whose attenuation coefficient is of similarly high value, for example, within a fixed percentage (e.g., 1% or 5% or 10%) of the value $x_i$. Such a group of voxels may be merged into one or several super-voxels. In another variant, the merging is only carried out if the group of voxels is surrounded by a further layer of voxels with similar attenuation coefficients, or by a further two layers thereof.

In practice, objects 110, and high density components such as bones or metal within those objects 110, are likely to have curvature at their boundaries. Furthermore, the boundaries of the voxels are unlikely to be aligned with the boundaries of such high density components, and in a situation in which a boundary extends only through part of a voxel, so that only part of the voxel is highly attenuating, it is possible that two different rays can pass through the voxel, one extending through the strongly attenuating part and the other through the weakly attenuating part. This would provide conflicting measurements for the voxel, so that it may not be possible to solve the system of equations, even when it is underdetermined, whereas the basis pursuit model is based on the assumption that the system has infinitely many solutions. The incorporation of an error term ε in the model partly addresses this problem, but the incompatibility of the linear system Ax=b can also be detected via standard numerical linear algebra procedures, and the causative voxels can be identified and locally refined. This provides a second mechanism for the amendment of the voxelization.

Boundaries of high density components of the object 110 may also cause the appearance of artifacts in the reconstructed values of the attenuation coefficients x. Such artifacts can be identified as voxels i with attenuation coefficients that are either much larger or much smaller in absolute value to the attenuation coefficients associated with the voxels surrounding them. Such voxels can be refined, thus providing a third mechanism for voxelization amendment.

More generally, since it is the boundaries of high density components that cause artifacts, numerical errors and inconsistencies, one can reduce these difficulties and thus increase the accuracy of the reconstruction by refining the voxelization in the vicinity of such boundaries. For this purpose, such boundaries have to be identified. This can be achieved in a number of ways: A first method is to treat the attenuation coefficient as a function of the spatial position and to compute a numerical approximation of the gradient of this function by finite differences, using the component of the vector x. Locations where the gradient has a large norm (e.g., as measured in the Euclidean norm) correspond to voxels that may lie on a boundary and should be refined. A second method consists of numerically estimating the Hessian matrix of this function at each of the voxels, using the components of x and the spatial information about voxel location for finite differencing, and to identify boundary voxels as locations where the Hessian is highly ill-conditioned. Furthermore, by this method, the rank of the Hessian at a boundary point reveals the dimension of the boundary structure. For example, if the Hession is rank deficient with approximate rank 2, the point lies on a 2-dimensional boundary structure, while if the Hessian is of approximate rank 1, the point lies on a filigrane boundary structure of dimension 1. In both cases the eigenvectors of the approximate Hessian reveal the directions in which the boundary structure is extended locally, corresponding to further points where the approximate Hessian has to be computed and analyzed. In practice, it is thus not necessary to compute and analyze an approximate Hessian at all voxels of the voxelization, but it suffices to identify boundary points via a simpler method and to use the method of approximate Hessians to extend and track the boundary structures some of whose points have already been identified. One example of a simple method for identifying potential boundary points is to establish a first set of voxels that are surrounded by voxels with attenuation coefficients of predetermined low absolute magnitudes, and a second set of voxels that are surrounded by voxels with attenuation coefficients of predetermined high absolute magnitudes, and then find any voxels that are within a predetermined distance of both sets (or equivalently, to extend the boundaries of both sets by half that predetermined distance, and identify those voxels (if any) that are in both extended sets).

The refinements of the voxelization enable a more accurate three-dimensional image to be obtained in the next outer iteration, while the coarsenings ensure that the design matrix and thus problem dimension of the instance of problem (13) solved in the next outer iteration does not grow excessively, thus keeping the complexity of the numerical computation within reasonable bounds, as determined by the nature of the computational resources employed for this computation and the need for the reconstruction speed determined by the intended application.

Although a system has been described with all the emitters mounted on a single flat panel and are all oriented in the same direction, wherein all the emitters in each group are capable of confining their respective output radiation cones onto respective non-overlapping areas of the detector array, it should be apparent to those skilled in the image reconstruction art that other configurations may be possible, as long as the relative positions of at least some of the emitters and detectors are fixed and known and the respective contributions of those fixed emitters to those fixed detectors can be determined. Furthermore, although the task of correlating the received radiation with particular points along the converging transmission paths from multiple detectors is simplified if each detector receives radiation from only one emitter at any given point in time, such a constraint is not absolute. If only a relatively few detectors are determined during the calibration process to be receiving substantial radiation from more than one emitter in the same group, then the combined output from a pair of adjacent emitters that is received at a particular location in the detector array can simply be allocated (or ignored) based on measurements made during system calibration.

While the invention has been described and illustrated herein, those of ordinary skill in the art will readily envision a variety of other means and/or structures for performing the functions and/or obtaining the results and/or one or more of the advantages described herein, and each of such variations or modifications is deemed to be within the scope of the present invention. More generally, those skilled in the art will readily appreciate that all parameters, dimensions, materials, and configurations described herein are meant to be exemplary and that the actual parameters, dimensions, materials, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and/or claimed. The present invention is directed to each individual feature, system, material and/or method described herein. In addition, any combination of two or more such features, systems, articles, materials and/or methods, if such features, systems, articles, materials and/or methods are not mutually inconsistent, is included within the scope of the present invention. Accordingly, the scope of the present invention is not intended to be limited to the exemplary embodiments described above, but only by the appended claims and such other claims (both new and amended) that may be added hereto prior to expiration of any rights based in whole or in part on this patent application. Moreover, such scope should not be interpreted as limited by the literal language of such claims, but rather is intended to include any obvious modifications or structural or functional equivalents thereto, both known and as yet unknown.

All definitions as used herein are solely for the purposes of this disclosure. These definitions should not necessarily be imputed to other commonly-owned patents and/or patent applications, whether related or unrelated to this disclosure. The definitions, as used herein, should be understood to control over dictionary definitions, definitions in documents incorporated by reference, and/or ordinary meanings of the defined terms.

The invention claimed is:

1. A digital x-ray imaging system comprising:
    a fixed 2-dimensional array of detectors supported in a fixed position relative to a fixed 2-dimensional array of emitters, the radiation from each emitter having a conical beam pattern covering a respective detector subarray, each detector receiving radiation from a respective emitter subarray and outputting a time-varying signal representative of the received radiation from those emitters,
    a controller for activating successive groups of the emitters such that each emitter group includes a two-dimensional combination of emitters having multiple associated beam patterns that collectively cover a respective two-dimensional combination of spatially separated detector subarrays; and
    a programmed digital processor for reconstructing from the successive individual outputs of the detector subarrays a three-dimensional image of a region of interest located between the emitter array and the detector array, said digital processor comprising:
    means for organizing the region of interest into a three-dimensional space divided into a plurality of three dimensional voxels, and using the successive individual outputs from the detectors and the known positions and activational sequences of the individual emitters in the emitter array to estimate the respective amounts of radiation absorbed along corresponding radiation paths from each emitter to each detector within the coverage of that emitter,
    means for using the absorbed radiation calculations and a known relationship between attenuation coefficients and absorbed radiation to identify radiation paths of interest having estimated absorbed radiation greater than a predetermined threshold and to calculate a respective attenuation coefficient for each voxel along each identified radiation path of interest and for refining the calculated attenuation coefficients to reduce any statistically significant differences between the calculated absorption and the measured absorption along each identified path of interest, and
    means for creating a modified voxel array with an improved discretization and reduced error by searching for voxels having an estimated attenuation coefficient that is dissimilar by a first threshold from the corresponding coefficients of at least one adjoining neighbor and dividing each such voxel into a respective pair of smaller voxels at varying distances from the respective adjoining neighbor, searching for pairs of adjoining voxels having respective attenuation coefficients that are similar within a second threshold and combining each such pair of adjoining voxels into a respective larger voxel, re-calculating absorption coefficients for at least any resulting smaller or larger voxels in the new voxel array, and repeating the above searching and re-calculating steps until the most recently modified voxel array does not qualify for further dividing or combining.

2. The digital x-ray imaging system of claim 1, wherein:
    the calculation of the absorption coefficients for at least some of the voxels takes into account not only the location and size of the voxel within the voxel array but also the location and angle at which a radiation ray defining a respective radiation path from a particular emitter to a particular detector enters and exits that voxel.

3. The digital x-ray imaging system of claim 1, wherein:
    at least the dividing operations are successively repeated until any further division of voxels would not further reduce the calculated error by a predetermined amount.

4. The digital x-ray imaging system of claim 1, wherein:
at least the combining operations are successively repeated until any further combination of voxels would increase the calculated error above a predetermined level of confidence.

5. The digital x-ray imaging system of claim 1, wherein:
at least the dividing operations are not repeated once any further combination of voxels would increase the size of the voxel array above a predetermined maximum.

6. The digital x-ray imaging system of claim 1, wherein:
the re-calculating and searching operations are repeated in iterative fashion for all voxels once there are no further candidate voxels for division or combination in a prior iteration.

7. The digital x-ray imaging system of claim 1, wherein:
the searching operations are repeated each time the re-calculating operation results in at least one revised attenuation coefficient that is materially different from a corresponding prior attenuation coefficient.

8. The digital x-ray imaging system of claim 1, wherein:
any boundary voxels within a predetermined distance of both a high-density region having a density above a predetermined upper limit and a low-density region having a density below a predetermined lower limit are identified, any resultant boundary region defined by those boundary voxels is refined, and the refined boundary region is flagged as possibly containing an artifact.

9. The digital x-ray imaging system of claim 1, wherein:
the resultant three-dimensional image is transformed into a specified series of two dimensional views.

10. The digital x-ray imaging system of claim 1, wherein:
the organization of emitters into groups is based on extended arrays of regular polygons such as squares or hexagons with the emitters in each group being associated with vertices or centers of individual polygons that are separated by a predetermined distance corresponding to the nominal diameter of the projected radiation cone, and with a similar organization of the other groups with respective predetermined offsets that are multiples of a fraction of that nominal diameter.

11. The digital x-ray imaging system of claim 1, wherein:
the radiation beam pattern of each emitter is estimated within a predetermined noise threshold by the digital processor during an initial calibration process in which the controller activates the emitters individually rather than in groups.

12. The digital x-ray imaging system of claim 11, wherein:
the initial calibration process includes placing a known 3D probe having known absorption coefficient data at a known location between the emitter array and the detector array, and comparing the resultant calculated image data with the corresponding known data.

13. The digital x-ray imaging system of claim 1, wherein:
the individual voxels are represented as three dimensional vectors or wavelets.

14. The digital x-ray imaging system of claim 1, wherein:
at least some of the individual voxels are organized in a hierarchical tree structure.

15. The digital x-ray imaging system of claim 1, wherein:
the calculation of the absorption coefficients for at least some of the voxels takes into account not only the location and size of the voxel within the voxel array but also the location and angle at which the radiation ray defining a respective radiation path from a particular emitter to a particular detector enters and exits that voxel.

16. The digital x-ray imaging system of claim 15, wherein:
the attenuation coefficients are calculated and refined in hierarchical fashion using compressed sensing algorithms.

17. The digital x-ray imaging system of claim 16, wherein:
the compressed sensing algorithms are known algorithms selected from the group consisting essentially of the simplex algorithm, Nesterov's smoothing algorithm, the YALL1 algorithm, and combinations thereof.

18. The digital x-ray imaging system of claim 15, wherein:
the attenuation coefficients are calculated and refined in hierarchical fashion using at least one algorithm or method selected from the group consisting essentially of simplex algorithms, interior point algorithms, sub-gradient algorithms, the ellipsoid method, bundle methods, the perceptron algorithm, Bregman-projection algorithms, Nesterov's smoothing algorithm, random-ized coordinate descent methods, Alternating Direction Algorithms, alternating block coordinate descent algorithms, forward-backward splitting and proximal methods, and variants and combinations thereof.

19. A digital x-ray imaging system comprising:
a fixed array of detectors supported in a fixed position relative to a fixed array of emitters, the radiation from each emitter having a conical beam pattern covering a respective detector subarray, each detector receiving radiation from a respective emitter subarray and outputting a time-varying signal representative of the received radiation from those emitters, a controller for activating successive groups of the emitters such that each emitter group includes a two-dimensional combination of emitters having multiple associated beam patterns that collectively cover a respective two-dimensional combination of spatially separated detector subarrays; and
a digital processor for reconstructing from the successive individual outputs of the detector subarrays a three-dimensional image of a region of interest located between the emitter array and the detector array, said digital processor comprising:
means for organizing the region of interest into a three-dimensional space divided into a plurality of three dimensional voxels,
means for using the successive individual outputs from the detectors and the
known positions and activational sequences of the individual emitters in the emitter array to estimate the respective amounts of radiation absorbed along corresponding radiation paths from each emitter to each detector within the coverage of that emitter,
means for using the absorbed radiation calculations to identify radiation paths of
interest having estimated absorbed radiation greater than a predetermined threshold and for using a known relationship between attenuation coefficients and absorbed radiation to calculate a respective attenuation coefficient for each voxel along each identified radiation path of interest,
means for refining the calculated attenuation coefficients to reduce any statistically significant differences between the calculated absorption and the measured absorption along each identified path of interest, and means for creating a modified voxel array with an improved discretization and reduced error by:

searching for voxels having an estimated attenuation coefficient that is dissimilar by a first threshold from the corresponding coefficients of at least one adjoining neighbor and dividing each such voxel into a respective pair of smaller voxels at varying distances from the respective adjoining neighbor, searching for pairs of adjoining voxels having respective attenuation coefficients that are similar within a second threshold and combining each such pair of adjoining voxels into a respective larger voxel, re-calculating absorption coefficients for at least any resulting smaller or larger voxels in the new voxel array, and repeating the above searching and re-calculating steps to create a newly modified voxel array from a previously modified voxel arrays until the most recently modified voxel array does not qualify for further dividing or combining, wherein:

calculation of the absorption coefficients for at least some of the voxels takes into account not only the location and size of the voxel within the voxel array but also the location and angle at which a radiation ray defining a respective radiation path from a particular emitter to a particular detector enters and exits that voxel, at least the dividing operations are successively repeated until any further division of voxels would not further reduce the calculated error by a predetermined amount, at least the combining operations are successively repeated until any further combination of voxels would increase the calculated error above a predetermined level of confidence, at least the dividing operations are not repeated once any further combination of voxels would increase the size of the voxel array above a predetermined maximum, the re-calculating and searching operations are repeated in iterative fashion for all voxels once there are no further candidate voxels for division or combination in a prior iteration, the searching operations are repeated each time the re-calculating operation results in at least one revised attenuation coefficient that is materially different from a corresponding prior attenuation coefficient, any boundary voxels within a predetermined distance of both a high density region having a density above a predetermined upper limit and a low density region having a density below a predetermined lower limit are identified, any resultant boundary region defined by those boundary voxels is refined, and the refined boundary region is flagged as possibly containing an artifact, the resultant three-dimensional image is transformed into a specified series of two-dimensional views, the radiation beam pattern of each emitter is estimated within a predetermined noise threshold by the digital processor during an initial calibration process in which the controller activates the emitters individually rather than in groups, and which includes placing a known 3D model having known absorption coefficient data at a known location between the emitter array and the detector array and comparing the resultant calculated image data with the corresponding known data.

20. The digital x-ray imaging system of claim 19, wherein:
the attenuation coefficients are calculated and refined in hierarchical fashion using compressed sensing algorithms.

21. The digital x-ray imaging system of claim 19, wherein:
the attenuation coefficients are further calculated and refined in hierarchical fashion using at least one algorithm or method selected from the group consisting essentially of simplex algorithms, interior point algorithms, subgradient algorithms, the ellipsoid method, bundle methods, the perceptron algorithm, Bregman-projection algorithms, Nesterov's smoothing algorithm, randomized coordinate descent methods, Alternating Direction Algorithms, alternating block coordinate descent algorithms, forward-backward splitting and proximal methods, and variants and combinations thereof.

22. The digital x-ray imaging system of claim 19, wherein:
the compressed sensing algorithms are known algorithms selected from the group consisting essentially of the simplex algorithm, Nesterov's smoothing algorithm, the YALL1 algorithm, and combinations thereof.

23. A method for constructing a two-dimensional x-ray image from a fixed array of detectors supported in a fixed position relative to a fixed array of emitters, the radiation from each emitter having a conical beam pattern covering a respective detector subarray, each detector receiving radiation from a respective emitter subarray and outputting a time-varying signal representative of the received radiation from those emitters, comprising the steps activating successive groups of the emitters such that each emitter group includes a two dimensional combination of emitters having multiple associated beam patterns that collectively cover a respective two dimensional combination of spatially separated detector subarrays;

reconstructing from the successive individual outputs of the detector subarrays a three-dimensional image of a region of interest located between the emitter array and the detector array by organizing the region of interest into a three-dimensional space divided into a plurality of three-dimensional voxels, using the successive individual outputs from the detectors and the known positions and activational sequences of the individual emitters in the emitter array to estimate the respective amounts of radiation absorbed along corresponding radiation paths from each emitter to each detector within the coverage of that emitter, using the absorbed radiation calculations to identify radiation paths of interest having estimated absorbed radiation greater than a predetermined threshold, using a known relationship between attenuation coefficients and absorbed radiation to calculate a respective attenuation coefficient for each voxel along each identified radiation path of interest, refining the calculated attenuation coefficients to reduce any statistically significant differences between the calculated absorption and the measured absorption along each identified path of interest, and creating a modified voxel array with an improved discretization and reduced error by:

searching for voxels having an estimated attenuation coefficient that is dissimilar by a first threshold from the corresponding coefficients of at least one adjoining neighbor and dividing each such voxel into a respective pair of smaller voxels at varying distances from the respective adjoining neighbor, searching for pairs of adjoining voxels having respective attenuation coefficients that are similar within a second threshold and combining each such pair of adjoining voxels into a respective larger voxel, re-calculating absorption coefficients for at least any resulting smaller or larger voxels in the modified voxel array, and repeating the above searching and re-calculating steps to create a newly modified voxel array from a previously modified voxel arrays until the most recently modified voxel array does not qualify for further dividing or combining.

24. The method of claim 23, wherein calculation of the absorption coefficients for at least some of the voxels takes into account not only the location and size of the voxel within the voxel array but also the location and angle at which a radiation ray defining a respective radiation path from a particular emitter to a particular detector enters and exits that voxel, the dividing operations are successively repeated until any further division of voxels would not further reduce the calculated error by a predetermined amount, the combining operations are successively repeated until any further combination of voxels would increase the calculated error above a predetermined level of confidence, the dividing operations are not repeated once any further combination of voxels would increase the size of the voxel array above a predetermined maximum, re-calculating and searching operations are repeated in iterative fashion for all voxels once there are no further candidate voxels for division or combination in a prior iteration, the searching operations are repeated each time the re-calculating operation results in at least one revised attenuation coefficient that is materially different from a corresponding prior attenuation coefficient, any boundary voxels within a predetermined distance of both a high density region having a density above a predetermined upper limit and a low density region having a density below a predetermined lower limit are identified, any resultant boundary region defined by those boundary voxels is refined, and the refined boundary region is flagged as possibly containing an artifact, the resultant three-dimensional image is transformed into a specified series of two dimensional views, the radiation beam pattern of each emitter is estimated within a predetermined noise threshold an initial calibration process in which the emitters are activated individually rather than in groups, the initial calibration process includes placing a known 3D model having known absorption coefficient data at a known location between the emitter array and the detector array, and comparing the resultant calculated image data with the corresponding known data, the calculation of the absorption coefficients for at least some of the voxels takes into account not only the location and size of the voxel within the voxel array but also the location and angle at which the radiation ray defining a respective radiation path from a particular emitter to a particular detector enters and exits that voxel.

25. The method of claim 24, wherein:

the attenuation coefficients are calculated and refined in hierarchical fashion using compressed sensing algorithms.

26. The digital x-ray imaging system of claim 24, wherein:

the attenuation coefficients are further calculated and refined in hierarchical fashion using at least one algorithm or method selected from the group consisting essentially of simplex algorithms, interior point algorithms, subgradient algorithms, the ellipsoid method, bundle methods, the perceptron algorithm, Bregman-projection algorithms, Nesterov's smoothing algorithm, randomized coordinate descent methods, Alternating Direction Algorithms, alternating block coordinate descent algorithms, forward-backward splitting and proximal methods, and variants and combinations thereof.

27. The digital x-ray imaging system of claim 24, wherein:

the compressed sensing algorithms are known algorithms selected from the group consisting essentially of the simplex algorithm, Nesterov's smoothing algorithm, the YALL1 algorithm, and combinations thereof.

* * * * *